United States Patent [19]

Ohnishi et al.

[11] Patent Number: 4,481,137

[45] Date of Patent: Nov. 6, 1984

[54] GLYCOPROTEINS AND PROCESSES FOR THEIR PRODUCTION

[75] Inventors: Haruo Ohnishi, Funabashi; Kazuo Yamaguchi, Koganei; Yasuo Suzuki, Kawaguchi; Ei Mochida; Nobuo Mochida, both of Tokyo, all of Japan

[73] Assignee: Mochida Pharmaceutical Co., Ltd., Tokyo, Japan

[21] Appl. No.: 467,840

[22] Filed: Feb. 18, 1983

[30] Foreign Application Priority Data

Feb. 26, 1982 [JP] Japan .................. 57-28992
Feb. 26, 1982 [JP] Japan .................. 57-28993
May 24, 1982 [JP] Japan .................. 57-87674
May 24, 1982 [JP] Japan .................. 57-87675
Jun. 23, 1982 [JP] Japan .................. 57-108046

[51] Int. Cl.$^3$ ............................................ C07G 7/00
[52] U.S. Cl. .................... 260/112 R; 424/95; 424/177
[58] Field of Search .............. 260/112 R; 424/177, 424/95

[56] References Cited

U.S. PATENT DOCUMENTS 4,243,582  1/1981  Spilburg et al. ............... 260/112 R
4,269,825  5/1981  Bohn et al. ..................... 424/85
4,275,056  6/1981  Tokaki et al. .................. 260/112 R

OTHER PUBLICATIONS

Identification and Partial Characterization of 5 Major . . . Glycoprotein . . . Fibroblasts, *J. Membrane Biol.* 53, 1980, Tarone et al., 55-61.

70,000 Molecular-Weight Protein Isolated . . . Disulfide Bridge . . . Structure, *Bio Chem I*, 197, 1981, Pearson et al.

Isolation and Partial Characterization of 72000 Glycoprotein . . . Antigen, *J. Immunol.*, 126(6), 1981, 2171, Ishi et al.

*Primary Examiner*—John Kight
*Assistant Examiner*—Garnette D. Draper
*Attorney, Agent, or Firm*—Parkhurst & Oliff

[57] ABSTRACT

A glycoprotein obtained from the cells of human or non-human warm-blooded animals having an anti-tumor effect and characterized by the following properties:

(a) molecular weight: in the range from 7,000 to 90,000 by Sephadex gel filtration or SDS gel electrophoresis;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 8–45%, 6–28% of the total sugar being hexoses, 1–11% being hexosamines and 1–6% being sialic acids;

(e) stability: stable in an aqueous solution of pH 2.0, pH 7.0 or pH 11.0 at 4° C. for 24 hours or longer and in an aqueous solution of pH 7.0 at 60° C. for 3 hours or longer; and (f) cytotoxicity: it selectively damages tumor cells without substantially damaging normal cells.

60 Claims, 4 Drawing Figures

GLYCOPROTEINS AND PROCESSES FOR THEIR PRODUCTION

BACKGROUND OF THE INVENTION

1. Field of the Invention

This invention relates to novel glycoproteins obtained from an extract or a supernatant of culture medium of reticulo-endothelial cells, lymphoblasts, leukemia cells or fibroblasts of warm-blooded animals, processes for their production and therapeutic agents for malignant tumors which contain such glycoproteins singly or in combination as an active ingredient.

2. Description of the Prior Art

There has been known no perfect therapy for tumors, and in spite of the fact that many therapeutic agents for tumors have hitherto been developed by a number of researchers in the world, there have been many attempts to use new therapeutic agents and multi-agent combination treatments in the clinical field.

Therapeutic agents for tumors are roughly classified into two categories, chemotherapeutic agents and immunotherapeutic agents. Chemotherapeutic agents, also known as cytotoxic substances, manifest their effect by nonspecifically suppressing cell growth and hence are toxic not only to tumor cells but also to normal cells, and show serious adverse reactions such as leukocytopenia, acyesis, alopecia, teratism, malignant neoplasms, etc.; consequently, there is a strict restriction on the dosage. On the other hand, since the immunotherapeutic agents manifest their therapeutic effect by indirectly inhibiting tumor growth through acting upon the biophylactic functions and not by directly inhibiting the growth of the tumor cells, there is far less danger for serious adverse reactions as compared with chemotherapeutic agents. However, tumor patients do not often retain enough biophylactic functions and therefore the therapeutic effect of immunotherapeutic agents is not always satisfactory as compared with that of chemotherapeutic agents.

The present inventors conceived that the reticulo-endothelial cells which play an important role in biophylactic functions produce a substance which is effective for treating tumors, and have been searching for this substance.

Several factors considered as promising therapeutic agents for tumors, e.g. Lymphotoxin, Tumor Necrosis Factor, Interferon, etc., have been obtained from reticulo-endothelial cells, as reported by Granger, G. A. et al., Cellular Immunology, Vol. 38, 338–402 (1978); Carswell, E. A. et al., Proc. Natl. Acad. Sci. U.S.A., Vol. 72, 3666–33670 (1975); and Issacs, A. et al., Proc. Roy. Soc. Ser. B., Vol. 147, 268 (1975), respectively. Further, the present inventors have recently discovered a simple method for isolating a large amount of Carcino-Breaking Factor (hereinafter referred to as CBF) as a mixture which contains the aforesaid Lymphotoxin, Tumor Necrosis Factor, etc. from a culture of lymphoblasts grown in hamsters whose immune response had been suppressed, and have reported that this CBF is effective against experimental tumors transplanted to an animal (The Yomiuri, morning issue, Nov. 22, 1981).

During the course of the research on CBF, the present inventors have discovered that glycoproteins which differ from the aforesaid cytotoxic factors such as Lymphotoxin, Tumor Necrosis Factor, CBF, etc. are present in an extract or a supernatant of culture medium of reticulo-endothelial cells, lymphoblasts, leukemia cells or fibroblasts of warm-blooded animals, and are characterized by a very strong and selective cytotoxic effect against tumor cells. The present inventors have also established several processes for producing such glycoproteins without difficulties.

SUMMARY OF THE INVENTION

An object of this invention is to provide novel glycoproteins having an anti-tumor activity.

Another object of this invention is to provide glycoproteins having an anti-tumor activity which are harvested from an extract or a supernatant of culture medium of reticulo-endothelial cells, lymphoblasts, leukemia cells or fibroblasts of warm-blooded animals.

A further object of this invention is to provide processes for producing anti-tumor glycoproteins from an extract or a supernatant of culture medium of reticulo-endothelial cells, lymphoblasts, leukemia cells or fibroblasts of warm-blooded animals.

A still further object of this invention is to provide therapeutic agents for tumors which contain such anti-tumor glycoproteins singly or in combination as an active ingredient.

Accordingly, this invention relates to a glycoprotein having the following properties:

(a) molecular weight: in the range from 7,000 to 90,000 by Sephadex gel filtration or SDS gel electrophoresis;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: while powder soluble in water, aqueous sodium chloride and phosphate buffer and sparingly soluble in benzene, hexane and chloroform;

(d) sugar content is 8–45%, 6–28% of the total sugar being hexoses, 1–11% being hexosamines and 1–6% being sialic acids;

(e) stable in an aqueous solution of pH 2.0, pH 7.0 or pH 11.0 at 4° C. for 24 hours or longer and in an aqueous solution of pH 7.0 at 60° C. for 3 hours or longer; and (f) it selectively damages tumor cells without substantially damaging normal cells.

DETAILED DESCRIPTION OF THE PREFERRED EMBODIMENTS

Figure 1:
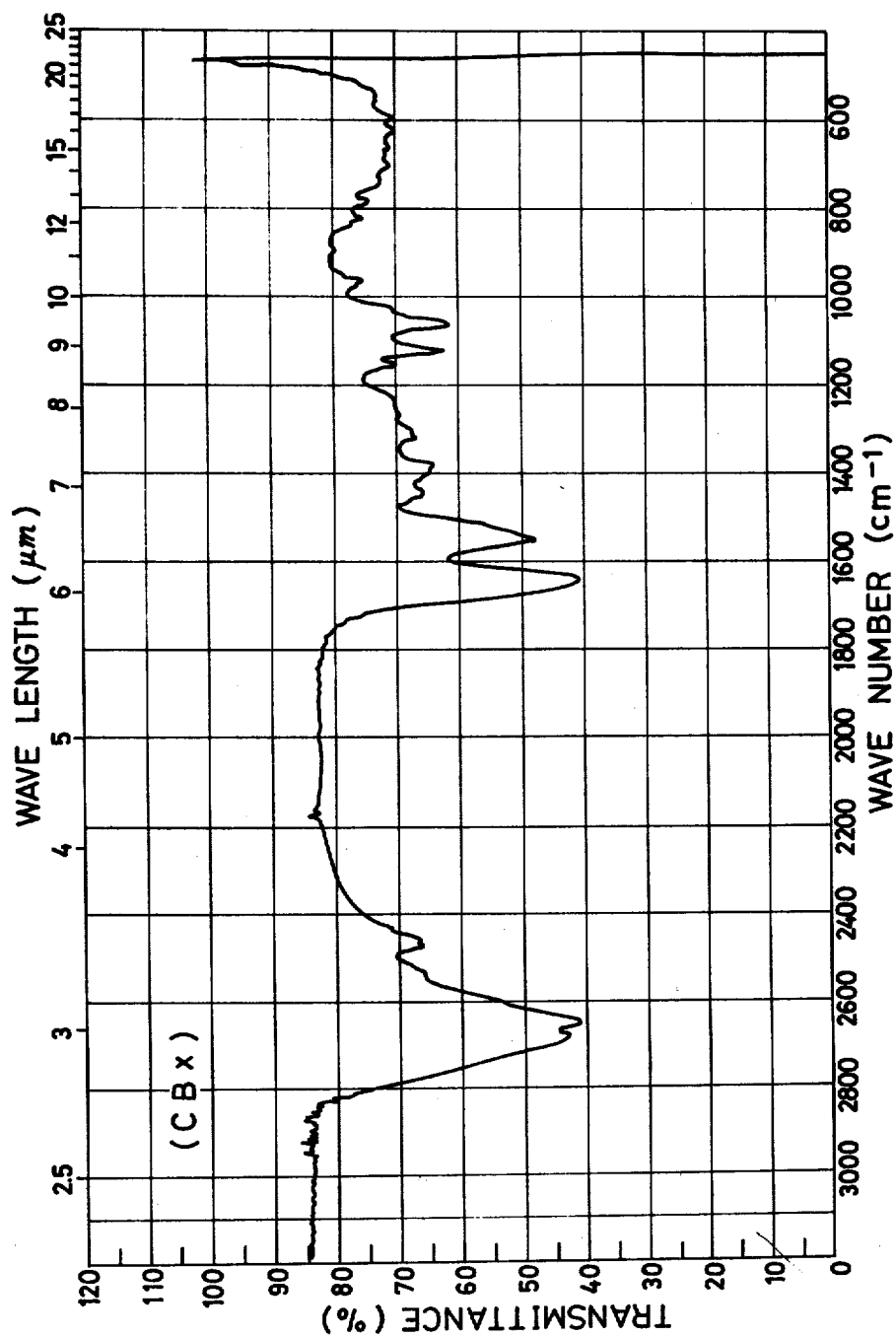
FIG. 1 shows the IR spectrum of $CB_X$ measured in Example 10.

Since the glycoproteins of this invention may be divided into four fractions with different molecular weights and sugar contents, these glycoproteins are classified according to the difference in molecular weight throughout the specification; one fraction with a molecular weight of 12,000–17,000 is referred to as Carcino-Breaker X (hereinafter referred to as $CB_X$; this also applies to the rest), one with a molecular weight of 70,000–90,000 as $CB_{X1}$, one with a molecular weight of 40,000–50,000 as $CB_{X2}$ and one with a molecular weight of 7,000–9,000 as $CB_{X3}$. Where all of $CB_X$, $CB_{X1}$, $CB_{X2}$ and $CB_{X3}$ are to be generally considered, "CB" is used as a general term therefor.

Physical, chemical and biological properties of glycoproteins of the invention $CB_X$ (a) Molecular weight: When measured by gel filtration using Sephadex G-100 (Pharmacia Co.) and 0.01M phosphate buffer (pH 7.2) as a solvent, the molecular weight is 12,000–17,000.

(b) Color reactions: The results of the tests on the $CB_X$ aqueous solution for color reactions are shown in Table 1-1. The Lowry reaction and the ninhydrin reaction were conducted according to the procedures described in Seikagaku Jikken Koza, Vol. 1, Quantitative Method of Proteins, 1971. The phenol-sulfuric acid reaction, the anthrone-sulfuric acid reaction, the naphthol-sulfuric acid reaction, the indole-sulfuric acid reaction and the tryptophane-sulfuric acid reaction were conducted according to the procedures described in Seikagaku Jikken Koza, Vol. 4, Quantitative Method of Sugars, 1971. The Holff reactions were conducted according to the procedures described in Seikagaku Jikken Koza, Vol. 3, Quantitative Method of Lipids, 1971.

TABLE 1-1

| Color Reaction | Color | Indication |
| --- | --- | --- |
| Lowry | Blue | Peptide bonds |
| Ninhydrin | Purple blue | Amino acids |
| Phenol-sulfuric acid | Brown | Sugars |
| Anthrone-Sulfuric acid | Greenish blue | Sugars |
| α-Naphthol-Sulfuric acid | Purple | Sugars |
| Indole-Sulfuric acid | Brown | Sugars |
| Tryptophane-Sulfuric acid | Purple brown | Sugars |
| Holff | Colorless | No lipids |

As shown above, $CB_X$ exhibits colors indicating proteins and sugars, but does not exhibit a color indicating lipids.

(c) Appearance and solubility: White powder soluble in water, aqueous sodium chloride and phosphate buffer, and sparingly soluble in benzene, hexane and chloroform.

(d) Sugar content: According to the method of Spiro (Spiro, H. A., Methods in Enzymology, Vol. 8, 3–26 (1966)), the sugar content of $CB_X$ is 27–33%, and its sugar composition is 17–20% of hexoses, 5–7% of hexosamines and 5–6% of sialic acids.

(e) Isoelectric point: When measured by isoelectrofocusing on Ampholine, its isoelectric point is 4.2–7.3.

(f) Adsorbability: Adsorbable on Ulex europeus agglutinin-conjugated Sephadex in 0.01M phosphate buffer (pH 7.2).

(g) Stability: Stable with respect to molecular weight by gel filtration and to cytotoxic activity against tumor cells in an aqueous solution of pH 2.0, pH 7.0 or pH 11.0 at 4° C. for 24 hours or longer and in an aqueous solution of pH 7.0 at 60° C. for 3 hours or longer.

(h) Cytotoxicity: It selectively damages tumor cells without substantially damaging normal cells.

The cytotoxicity of $CB_X$ was measured by culturing $10^5$ cells of tumor cells or normal cells in 0.2 ml of a medium in the presence of this substance at 37° C. for 48 hours in a 5% $CO_2$, 95% air atmosphere, and counting the number of viable cells not stained with Trypan Blue, and expressed by the concentration at which increase of the cells in number was inhibited by 50%. One unit of CB is defined to be the amount of the substance at which the growth of $10^5$ nasopharynx cancer of KB cell is inhibited by 50%.

(i) Differentiation: Induces differentiation of tumor cells, that is, recovers the tumor cells to normal cells in a test according to the method of Hozumi et al (Hozumi, et al., Cancer Research, Vol. 40, 2919–2924 (1980)), employing myelogenous leukemia cells M-1.

$CB_{X1}$ (a) Molecular weight: When measured by gel filtration using Sephadex G-100 and 0.01M phosphate buffer (pH 7.2) as a solvent, the molecular weight is 70,000–90,000.

(b) Color reactions: The results of the tests on the $CB_{X1}$ aqueous solution for color reactions are shown in Table 1-2.

TABLE 1-2

| Color Reaction | Color | Indication |
| --- | --- | --- |
| Lowry | Blue | Peptide bonds |
| Ninhydrin | Purple blue | Amino acids |
| Phenol-sulfuric acid | Brown | Sugars |
| Anthrone-Sulfuric acid | Greenish blue | Sugars |
| α-Naphthol-Sulfuric acid | Purple | Sugars |
| Indole-Sulfuric acid | Brown | Sugars |
| Tryptophane-Sulfuric acid | Purple brown | Sugars |
| Holff | Colorless | No lipids |

As shown above, $CB_{X1}$ exhibits colors indicating proteins and sugars, but does not exhibit a color indicating lipids.

(c) Appearance and solubility: White powder soluble in water, aqueous sodium chloride and phosphate buffer, and sparingly soluble in benzene, hexane and chloroform.

(d) Sugar content: According to the method of Spiro, supra, the sugar content of $CB_{X1}$ is 35–45%, and its sugar composition is 23–28% of hexoses, 8–11% of hexosamines and 4–6% of sialic acids.

(e) Isoelectric point: When measured by isoelectrofocusing on Ampholine, its isoelectric point is 4.3–6.2.

(f) Adsorbability: Adsorbable on Ulex europeus agglutinin-conjugated Sephadex in 0.01M phosphate buffer (pH 7.2).

(g) Stability: Stable with respect to molecular weight by gel filtration and to cytotoxic activity against tumor cells in an aqueous solution of pH 2.0, pH 7.0 or pH 11.0 at 4° C. for 24 hours or longer and in an aqueous solution of pH 7.0 at 60° C. for 3 hours or longer.

(h) Cytotoxicity: It selectively damages tumor cells without substantially damaging normal cells. The cytotoxicity of $CB_{X1}$ was measured by procedures described with respect to $CB_X$.

$CB_{X2}$ (a) Molecular weight: When measured by gel filtration using Sephadex G-100 and 0.01M phosphate buffer (pH 7.2) as a solvent, the molecular weight is 40,000–50,000.

(b) Color reactions: The results of the tests on the $CB_{X2}$ aqueous solution for color reactions are shown in Table 1-3.

TABLE 1-3

| Color Reaction | Color | Indication |
| --- | --- | --- |
| Lowry | Blue | Peptide bonds |
| Ninhydrin | Purple blue | Amino acids |
| Phenol-sulfuric acid | Brown | Sugars |
| Anthrone-Sulfuric acid | Greenish blue | Sugars |
| α-Naphthol-Sulfuric acid | Purple | Sugars |
| Indole-Sulfuric acid | Brown | Sugars |
| Tryptophane-Sulfuric acid | Purple brown | Sugars |
| Holff | Colorless | No lipids |

As shown above, $CB_{X2}$ exhibits colors indicating proteins and sugars, but does not exhibit a color indicating lipids.

(c) Appearance and solubility: White powder soluble in water, aqueous sodium chloride and phosphate buffer, and sparingly soluble in benzene, hexane and chloroform.

(d) Sugar content: According to the method of Spiro, supra, the sugar content of $CB_{X2}$ is 30–37%, and its sugar composition is 20–23% of hexoses, 6–8% of hexosamines and 4–6% of sialic acids.

(e) Isoelectric point: When measured by isoelectrofocusing an Ampholine, its isoelectric point is 4.2–7.3.

(f) Adsorbability: Adsorbable on Ulex europeus agglutinin-conjugated Sephadex in 0.01M phosphate buffer (pH 7.2).

(g) Stability: Stable with respect to molecular weight by gel filtration and to cytotoxic activity against tumor cells in an aqueous solution of pH 2.0, pH 7.0 or pH 11.0 at 4° C. for 24 hours or longer and in an aqueous solution of pH 7.0 at 60° C. for 3 hours or longer.

(h) Cytotoxicity: It selectively damages tumor cells without substantially damaging normal cells. The cytotoxicity of $CB_{X2}$ was measured by procedures described with respect to $CB_X$.

$CB_{X3}$ (a) Molecular weight: When measured by SDS gel electrophoresis, the molecular weight is 7,000–9,000.

(b) Color reactions: The results of the tests on the $CB_{X3}$ aqueous solution for color reactions are shown in Table 1-4.

TABLE 1-4

| Color Reaction | Color | Indication |
| --- | --- | --- |
| Lowry | Blue | Peptide bonds |
| Ninhydrin | Purple blue | Amino acids |
| Phenol-sulfuric acid | Brown | Sugars |
| Anthrone-Sulfuric acid | Greenish blue | Sugars |
| α-Naphthol-Sulfuric acid | Purple | Sugars |
| Indole-Sulfuric acid | Brown | Sugars |
| Tryptophane-Sulfuric acid | Purple brown | Sugars |
| Holff | Colorless | No lipids |

As shown above, $CB_{X3}$ exhibits colors indicating proteins and sugars, but does not exhibit a color indicating lipids.

(c) Appearance and solubility: White powder soluble in water, aqueous sodium chloride and phosphate buffer, and sparingly soluble in benzene, hexane and chloroform.

(d) Sugar content: According to the method of Spiro, supra, the sugar content of $CB_{X3}$ is 8–15%, and its sugar composition is 6–10% of hexoses, 1–2% of hexosamines and 1–3% of sialic acids.

(e) Adsorbability: Adsorbable on carboxymethylcellulose in an ion exchange chromatography in 0.05M phosphate buffer (PH 6.4) using carboxymethylcellulose.

(f) Stability: Stable with respect to molecular weight by gel filtration and cytotoxic activity agaist tumor cells in an aqueous solution of pH 2.0, pH 7.0 or pH 11.0 at 4° C. for 24 hours or longer and in an aqueous solution of pH 7.0 at 60° C. for 3 hours or longer.

(g) Cytotoxicity: It selectively damages tumor cells without substantially damaging normal cells. The cytotoxicity of $CB_{X3}$ was measured by the procedures described with respect to $CB_X$.

(h) The amino acid sequence of the N terminal of the protein portion is Alanine-Alanine-.

The glycoproteins of this invention have common characteristics in color reactions, appearance, solubility, stability, effect on tumor cells, etc., but they differ from each other with respect to molecular weight and sugar content, and therefore the respective substances may be distinguished from one another.

The glycoproteins of this invention are clearly distinguished from Lymphotoxin, Tumor Necrosis Factor, a mixture thereof (i.e. CBF) or Interferon, all of which are obtained from reticulo-endothelial cells, lymphoblasts, leukemia cells or fibroblasts, with regard to the following features. Thus they are evidently different substances.

More specifically, Lymphotoxin is known to be present in three different types depending on the molecular weight, i.e. α-Lymphotoxin having a molecular weight of 70,000–90,000, β-Lymphotoxin having a molecular weight of 35,000–50,000 and γ-Lymphotoxin having a molecular weight of 10,000–20,000 (Eds., Cohen et al., Biology of the Lymphokinase, Academic Press, 1979). With respect to the molecular weight, $CB_X$ resembles γ-Lymphotoxin, $CB_{X1}$ resembles α-Lymphotoxin and $CB_{X2}$ resembles β-Lymphotoxin. However, Lymphotoxin, as reported by Lucas et al (Lucas, Z. J. et al., J. Immunology, Vol. 109, 1233 (1972)), has little selectivity in cytotoxic effect and causes damage to normal cells as well as to tumor cells. In contrast, the cytotoxic effect of the glycoproteins of this invention is selective to tumor cells, and thus they are clearly different from Lymphotoxin. Moreover, the glycoproteins of this invention are different from Lymphotoxin in adsorbability and stability. More specifically, while Lymphotoxin prepared according to the method of Granger et al (Granger, G. A. et al, Cellular Immunology, Vol. 38, 388–402 (1978)) is not or only weakly adsorbed on Ulex europeus agglutinin-conjugated Sephadex in 0.01M phosphate buffer, the glycoproteins of this invention are adsorbed thereon. Furthermore, the glycoproteins of this invention are stable in aqueous solutions of pH 2.0, pH 7.0 and pH 11.0 at 4° C. for 24 hours or longer, and also are stable at pH 7.0 at 60° C. for 3 hours or longer. In constrast, Lymphotoxin loses its activity by 60% or more after it is maintained at 56° C. for 4 hours.

Tumor Necrosis Factor exhibits a selective cytotoxic effect on tumor cells, and it has a molecular weight of 33,000–63,000 and a sugar content of 0% (Carswell, E. A. et al, Proc. Natl. Acad. Sci. U.S.A., Vol. 72, 3666-3670 (1975)) or it has a molecular weight of 39,000 and a sugar content of 40% (The Nippon Keizai Shimbun, Morning issue, Aug. 23, 1981). Both are different from $CB_X$, $CB_{X1}$ and $CB_{X3}$ with respect to molecular weight and from $CB_{X2}$ with respect to sugar content.

Further, CBF, which contains these cytotoxic factors in combination, has a molecular weight of about 35,000 (The Nippon Keizai Shimbun, Morning Issue, Nov. 22, 1981) and differs from the glycoproteins of this invention with respect to molecular weight.

Finally, the glycoproteins of this invention are different from Interferon in that the former do not possess antiviral activity.

Cells employed for producing glycoproteins of the invention

The source cells originated from human or non-human warm-blooded animals for use in this invention may be any of reticuloendothelial cells, lymphoblasts, leukemia cells and fibroblasts, and they may be employed either in a primary culture or in an established cell line. Preferably, cells of human origin are desirable and safe because they elicit fewer antigenicity induced reactions and other adverse reactions with respect to use of CB in the treatment of human diseases. As such cells, any cells may be chosen from, for example, BALL-1 cells, TALL-1 cells and NALL-1 cells reported by Miyoshi (Miyoshi, I., Nature, Vol. 267, 843–844 (1977)), Namalwa cells described in Journal of Clinical Microbiology (J. Clin. Microbiol., Vol. 1, 116–117 (1975)), M-7002 cells and B-7101 cells described in Journal of Immunology (Vol. 113, 1334–1345 (1974)), Flow 7000 cells (Flow Co.), JBL cells, EBV-Sa cells, EBV-Wa cells and EBV-HO cells described in "The Tissue Culture" (Vol. 6, 527–546 (1980)), established cell lines such as BALM 2 cells, CCRF-SB cells (ATCC CCL 120) etc., human lymphocytes and macrophages, as well as the cells of an established cell line from human lymphocytes and macrophages treated with various viruses, drugs, radiation, etc.

As the source cells originated from non-human warm-blooded animals, any cells may be chosen from, for example, mouse BALB/C 3T3 cells (Flow Co.), mouse leukemia cells such as L1210 cells (J. Natl. Cancer Inst., Vol. 13, 1328 (1953)) and P388 cells (Scientific Proceedings, Pathologists & Bacteriologists, Vol. 33, 603 (1957)), mouse melanoma clone M-3 (Flow Co.), rat tumor LLC-WRC 256 (Flow Co.), hamster melanoma RPMI 1846 cells (Flow Co.), and lymphocytes, macrophages, etc. It should be understood that the cells which may be employed in this invention are not restricted to those described above.

Process for producing glycoproteins (CB) of the invention

The process for producing CB by cells originated from human or non-human warm-blooded animals may be chosen from known methods for producing active substances from cells, and it may be harvested either directly from the cells or after the cells have been cultured, or, if a larger amount of CB is desired, the cells may be exposed to one or more inducers. For example, the cells originated from human or non-human warm-blooded animals may be suspended in an appropriate medium and directly exposed to inducer to produce CB which may then be harvested from the medium.

As the inducer for CB, generally one or more substances chosen from the following may be used: lectins such as phytohemagglutinin, concanavalin A, pokeweed mitogen, lypopolysaccharides, polysaccharides such as phosphommanan, dextran phosphate, endotoxins, microbial cell components, bacteria, viruses, nucleic acids, polynucleotides, etc. Further, for the antigen-sensitized cells, corresponding antigens also serve as inducers for CB.

CB thus produced may be easily isolated by known purification methods, such as salting out, dialysis, filtration, centrifugation, concentration, lyophilization, etc. If higher purification is desired, it may be achieved by adsorption and elution on an ion exchange resin, gel filtration, electrophoresis or affinity chromatography using, for example, antibody- or Ulex europeus agglutinin-conjugated Sephadex.

If CB is to be obtained in a large quantity, the cells of the established cell line may be grown in the body of warm-blooded animals as is now explained.

The established cell lines originated from human or non-human warm-blooded animals may be any of reticuloendothelial cells, lymphoblasts, leukemia cells and fibroblasts. Cell lines of human origin are especially desirable and safe because they elicit fewer antigenicity induced reactions and other adverse reactions with respect to use of CB in the treatment of human diseases. As such cell lines, any cell lines may be employed, as described above, for example, BALL-1 cells, TALL-1 cells, NALL-1 cells, Namalwa cells, M-7002 cells, B-7101 cells, Flow 7000 cells, BALB/C 3T3 cells, L1210 cells, P388 cells, lymphocytes, macrophages, etc.

When these cells are to be grown in warm-blooded animals' bodies, transplantation of such cells may be carried out directly or, as described hereinbelow, indirectly by inoculating a chamber with said cells and placing the chamber into the body. The warm-blooded animals into which such cells are transplanted may be of the same or different species as long as the established cell line originated from human or non-human warm-blooded animals can grow therein. For example, fowls such as chickens and pigeons and mammals such as dogs, cats, monkeys, goats, pigs, horses, bovines, rabbits, guinea pigs, rats, hamsters, ordinary mice, or nude mice may be employed.

When cultured cells originated from an animal of different species are transplanted into one of these animals, there is a possibility of undesirable immunological reactions. Therefore, animals in the most immature state, e.g. eggs, foetuses, embryos, or onatals or infant animals, are suitably employed so that the possibility of immunological reactions is minimized. In addition, the immunological reactions may also be suppressed by pre-treatments, for example, by exposing these animals to X-ray of 200–600 REM, or injecting them with immunosuppressive agents.

When the animal to be used as the host is a nude mouse or of the same species as the source of cells to be transplanted, immunological reactions are weak and therefore such cells may be transplanted thereinto and grown rapidly without any pretreatment, and therefore the use of such cells is especially convenient.

Alternatively, constant growth of the cells may also be assured and the amount of CB produced therefrom may be increased by transplanting cells from one warm-blooded animal to another warm-blooded animal, for example, by transplanting cells originated from human or non-human warm-blooded animals into hamsters for growth and then retransplanting said cells into nude mice. In such cases, transplantation may be conducted between the same class or division as well as between the same species or genus.

The site to which the cells originated from human or non-human warm-blooded animals are to be transplanted may be any site where the transplanted cells can grow, for example the allantoic cavity, veins, the abdominal cavity, or subcutaneous sites may be freely chosen.

Instead of directly transplanting and growing established cell lines originated from human or non-human warm-blooded animals in the body of warm-blooded animals, any of the above mentioned established cell lines may be inoculated and grown in a conventional diffusion chamber of various shapes and sizes which is placed, for example, in the peritoneal cavity of the body of a warm-blooded animal. The diffusion chamber is designed to enable said cells to grow by facilitating the uptake of body fluid of the animal as nutrients. The chamber is also provided with porous filter membranes, for example, membrane filters with pore sizes of about $10^{-7}$–$10^{-3}$ m, ultrafilters or hollow fibers, which prevent the migration of cells out of the chamber and allow the body fluid as nutrients to enter the chamber.

If necessary, the diffusion chamber may be designed and placed, for example, on the surface of the animal body, so as to connect the nutrient fluid in the chamber with the body fluid of the animal and circulate them, so that the growth of the cells inoculated in said chamber can be observed through a view window. The diffusion chamber can also be designed so that it can be disconnected from the animal body, enabling cells to be grown over the whole life span of the animal, thus increasing the yield of cells per animal.

The method involving the use of these diffusion chambers has further advantages; that is, since the cells of the established cell lines originated from human or non-human warm-blooded animals are not brought into direct contact with the animal cells, such cells may be easily harvested. Because of the lower possibility of causing undesirable immunological reactions, various warm-blooded animals can be used without the need for pre-treatment of the animals for immunosuppression.

The animals to which the cells have been transplanted may be fed and maintained in the usual way for the animal, and no special care is required even after transplantation, a very convenient feature.

The period required for growth of the cells of the established cell lines originated from human or non-human warm-blooded animals is generally 1–10 weeks. The number of cells thus obtained has been found to be about $10^7$–$10^{12}$ cells or more per animal.

In other words, the process according to this invention for producing CB is extremely advantageous for producing CB, because the established cell lines originated from warm-blooded animals are multiplied by about $10^2$–$10^7$ fold or more over the number of the cells directly inoculated to animal, or about $10$–$10^8$ fold or more compared to the case wherein the cells were cultured in a nutrient medium.

The production of CB from the grown cells of an established cell line originated from human or non-human warm-blooded animals may be conducted in various manners. They may also be harvested directly from the body in which such cells have been grown. For example, CB may be harvested directly from the cells obtained by growing the transplanted cells of the established cell lines originated from human or non-human warm-blooded animals in ascites as a suspension or by growing them subcutaneously.

Alternatively, the production of CB may be conducted by using an inducer after growing the established cell lines originated from human or non-human warm-blooded animals in the body of an animal by applying the inducer either directly in vivo or in vitro after taking the cells out of the body. For example, the cells of an established cell line originated from human or non-human warm-blooded animals, which have been grown in ascites and harvested therefrom, or those isolated and dissociated from a subcutaneous tumor comprising the cells of an established cell line originated from human or non-human warm-blooded animals, may be suspended in a nutrient medium kept at about 20°–40° C. to give a cell concentration of about $10^5$–$10^8$ cells per ml, and then exposed to a CB inducer, thereby inducing the production of CB which may then be harvested.

Further, where the cells of an established cell line originated from human or non-human warm-blooded animals are grown in a diffusion chamber, the cells may be directly harvested from the chamber, of they may be harvested after once removing from the chamber either directly or even after exposure to one or more inducers.

Furthermore, the yield of CB per animal may be even further increased by employing, for example, the following methods: a method wherein the cells of an established cell line originated from human or non-human warm-blooded animals which have been grown in the body of another animal are exposed to an inducer to induce the production of CB in situ, and then the grown cells, which have been harvested from a specific site or the whole of the same animal body, are exposed to an inducer to induce the production of CB; a method wherein the used cells are again exposed to an inducer to induce the production of CB; a method wherein a diffusion chamber placed in or connected to the animal body is replaced by a new one to increase the number of the obtained cells; and the like.

For inducing the production of CB, any inducer for CB described above may be employed, and the thus produced CB may be fractionated into the respective $CB_X$, $CB_{X1}$, $CB_{X2}$ and $CB_{X3}$ having the specified molecular weights by using the above-described known separating and purifying procedures.

Effectiveness, toxicity, method of use and dosage of CB of the invention

Experiment 1: Selectivity of the Cytotoxic Effect

Samples of $10^5$ cells of each of tumor cell lines including KB cells (nasopharynx cancer), MX-1 cells (breast cancer, supplied from Dr. Shigeru Tsukagoshi, Cancer Institute), HEp-2 cells (throat cancer) and HEL cells (hepatoma, Flow Co.) and of normal cell lines including intestine 407 cells, Girardi heart cells, Chang Liver cells, Vero cells (monkey kidney) and MDCK cells (dog kidney) (Flow Co.), all of which had been precultured for 24 hours respectively, and $10^5$ cells of each of P388 and L1210 cells (leukemia, supplied from Dr. Shigeru Tsukagoshi, Cancer Institute), which were used immediately, were each cultured in 1 ml of Eagle's medium containing 10% calf serum and each test substance at 37° C. for 48 hours in a 5% $CO_2$, 95% air atmosphere. Thereafter the number of the viable cells not stained by Trypan Blue was counted under a light microscope, and the concentration of the test substance at which 50% of the cells are killed was calculated against a control taken as 100. Employed as the test substances were $CB_X$ obtained in Example 10, $CB_{X1}$ obtained in Example 16, $CB_{X2}$ obtained in Example 20, $CB_{X3}$ obtained in Example 26 or 29, mixture of $CB_X$ and $CB_{X1}$, mixture of $CB_X$, $CB_{X1}$, $CB_{X2}$ and $CB_{X3}$, mixture of $CB_{X2}$ and $CB_{X3}$, α-, β- and γ-Lymphotoxins obtained by a known method (Granger, G. A. et al, Cellular Immunology, Vol. 38, 388–402 (1978)), CBF separated from $CB_X$ in Example 1 and Mitomycin C. One unit of the Lymphotoxins and CBF is expressed by a conventional index which is based on the cytotoxicity on mouse L cells (Eds., Bloom, B. R. & Grade, P. R. "In Vitro Methods in Cell-mediated Immunity", Academic Press, 1979). The results are shown in Tables 2-1 to 2-4.

TABLE 2-1

| | Cell Name | Species | Concentration for 50% Inhibition of Growth | | | |
|---|---|---|---|---|---|---|
| | | | $CB_X$ (unit/ml) | γ-Lympho-toxin (unit/ml) | CBF (unit/ml) | Mitomycin C (μg/ml) |
| Tumor Cells | KB | Human | 1.0 | 16 | 18 | 34 |
| | HEp-2 | Human | 1.6 | 5.6 | 24 | 17 |
| | HEL | Human | 1.1 | — | 33 | 26 |
| | MX-1 | Human | 1.9 | — | 3.5 | 32 |
| | L1210 | Mouse | 3.0 | — | — | 43 |
| | P388 | Mouse | 3.3 | — | — | 36 |
| Normal Cells | Intestine 407 | Human | >1,000 | 80.0 | >20,000 | 32 |
| | Girardi Heart | Human | >1,000 | — | >20,000 | 45 |
| | Chang Liver | Human | >1,000 | 8.0 | >20,000 | 19 |
| | Vero | Monkey | 650 | — | — | 52 |
| | MDCK | Dog | 520 | — | — | 41 |

(Note)
"—" means the experiment has not been conducted.

TABLE 2-2

| | Cell Name | Species | Concentration for 50% Inhibition of Growth | | | | | |
|---|---|---|---|---|---|---|---|---|
| | | | $CB_{X1}$ (unit/ml) | $CB_{X2}$ (unit/ml) | α-Lympho-toxin (unit/ml) | β-Lympho-toxin (unit/ml) | CBF (unit/ml) | Mitomycin C (μg/ml) |
| Tumor Cells | KB | Human | 1.0 | 1.0 | 19 | 21 | 18 | 34 |
| | Hep-2 | Human | 1.5 | 1.4 | 4.8 | 7.2 | 24 | 17 |
| | HEL | Human | 1.3 | 1.5 | — | — | 33 | 26 |
| | MX-1 | Human | 1.8 | 1.6 | — | — | 3.5 | 32 |
| | L1210 | Mouse | 3.2 | 3.4 | — | — | — | 43 |
| | P388 | Mouse | 3.2 | 3.2 | — | — | — | 36 |
| Normal Cells | Intestine 407 | Human | >1,000 | >1,000 | 76.0 | 92.0 | >20,000 | 32 |
| | Girardi Heart | Human | >1,000 | >1,000 | — | — | >20,000 | 19 |
| | Chang Liver | Human | >1,000 | >1,000 | 9.6 | 8.8 | >20,000 | 19 |
| | Vero | Monkey | 630 | 640 | — | — | — | 52 |
| | MDCK | Dog | 550 | 530 | — | — | — | 41 |

(Note)
"—" means the experiment has not been conducted.

TABLE 2-3

| | Cell Name | Species | Concentration for 50% Inhibition of Growth | | |
|---|---|---|---|---|---|
| | | | $CB_{X3}$*(1) (unit/ml) | $CB_{X3}$*(2) (unit/ml) | Mitomycin C (μg/ml) |
| Tumor Cells | KB | Human | 1.0 | 1.0 | 35 |
| | HEp-2 | Human | 1.5 | 1.7 | 18 |
| | HEL | Human | 1.3 | 1.4 | 25 |
| | MX-1 | Human | 1.8 | 1.7 | 30 |
| | L1210 | Mouse | 3.1 | 2.9 | 44 |
| | P388 | Mouse | 3.4 | 3.5 | 37 |
| Normal Cells | Intestine 407 | Human | >1,000 | >1,000 | 35 |
| | Girardi Heart | Human | >1,000 | >1,000 | 44 |
| | Chang Liver | Human | >1,000 | >1,000 | 21 |
| | Vero | Monkey | 620 | 580 | 50 |
| | MDCK | Dog | 510 | 540 | 44 |
| | Primary Culture Rat Liver | Rat | 870 | 910 | 61 |

(Notes)
*(1)$CB_{X3}$ obtained in Example 26
*(2)$CB_{X3}$ obtained in Example 29

TABLE 2-4

| | Cell Name | Species | Concentration for 50% Inhibition of Growth | | |
|---|---|---|---|---|---|
| | | | A*(1) (unit/ml) | B*(2) (unit/ml) | C*(3) (unit/ml) |
| Tumor Cells | KB | Human | 1.0 | 1.0 | 1.0 |
| | HEp-2 | Human | 1.5 | 1.4 | 1.6 |
| | HEL | Human | 1.6 | 1.7 | 1.9 |
| | MX-1 | Human | 1.8 | 1.7 | 1.6 |
| | L1210 | Mouse | 3.0 | 3.2 | 3.0 |
| | P388 | Mouse | 3.1 | 3.4 | 3.2 |
| Normal Cells | Intestine 407 | Human | >1,000 | >1,000 | >1,000 |
| | Girardi Heart | Human | >1,000 | >1,000 | >1,000 |
| | Chang Liver | Human | >1,000 | >1,000 | >1,000 |
| | Vero | Monkey | 610 | 590 | 580 |

TABLE 2-4-continued

| Cell Name | Species | Concentration for 50% Inhibition of Growth | | |
|---|---|---|---|---|
| | | $A^{*(1)}$ (unit/ml) | $B^{*(2)}$ (unit/ml) | $C^{*(3)}$ (unit/ml) |
| MDCK | Dog | 580 | 610 | 600 |

(Notes)
*(1)Mixture of $CB_X$ and $CB_{X1}$
*(2)Mixture of $CB_X$, $CB_{X1}$, $CB_{X2}$ and $CB_{X3}$
*(3)Mixture of $CB_{X2}$ and $CB_{X3}$ As evident from the above results, CB similar to CBF selectively damages tumor cells without substantially causing any damage to the normal cells. However, the intensities of the cytotoxic effect on the respective tumors were different between CB and CBF. In contrast, both α- and β-Lymphotoxin and Mitomycin C showed a nonselective cytotoxicity to the normal cells and the tumor cells.

Experiment 2: Influence on mice transplanted with Sarcoma 180 or Ehrlich Tumor

Male mice (ddY-Strain) weighing 25–30 g were intraperitoneally transplanted with $3 \times 10^6$ cells per animal of Sarcoma 180 or Ehrlich ascites tumor and the period of survival in days was observed. $CB_X$ obtained in Example 6, $CB_{X1}$ obtained in Example 15, $CB_{X2}$ obtained in Example 20 and $CB_{X3}$ obtained in Example 26 or 29 were intravenously administered to groups of 5 mice daily from one day after transplantation until death. The results are expressed in percentages of the average survival days to that of the control group and shown in Tables 3-1 to 3-3.

TABLE 3-1

| Tumor | Test Substance | Daily Dose | Average Survival Days (%) |
|---|---|---|---|
| Mouse Sarcoma 180 | $CB_X$ | 1.2 unit/kg | 111 |
| | | 4 unit/kg | 131 |
| | | 12 unit/kg | 164 |
| | Mitomycin C | 0.5 mg/kg | 140 |
| | Cyclophosphamide | 20 mg/kg | 172 |
| Ehrlich Ascites Tumor | $CB_X$ | 1.2 unit/kg | 141 |
| | | 4 unit/kg | 159 |
| | | 12 unit/kg | 187 |
| | Mitomycin C | 0.5 mg/kg | 168 |
| | Cyclophosphamide | 20 mg/kg | 212 |

TABLE 3-2

| Tumor | Test Substance | Daily Dose | Average Survival Days (%) |
|---|---|---|---|
| Mouse Sarcoma 180 | $CB_{X1}$ | 1 unit/kg | 113 |
| | | 3 unit/kg | 133 |
| | | 10 unit/kg | 160 |
| | $CB_{X2}$ | 1 unit/kg | 110 |
| | | 3 unit/kg | 135 |
| | | 10 unit/kg | 159 |
| | Mitomycin C | 0.5 mg/kg | 138 |
| | Cyclophosphamide | 20 mg/kg | 170 |
| Ehrlich Ascites Tumor | $CB_{X1}$ | 1 unit/kg | 139 |
| | | 3 unit/kg | 164 |
| | | 10 unit/kg | 187 |
| | $CB_{X2}$ | 1 unit/kg | 135 |
| | | 3 unit/kg | 161 |
| | | 10 unit/kg | 189 |
| | Mitomycin C | 0.5 mg/kg | 164 |
| | Cyclophosphamide | 20 mg/kg | 206 |

TABLE 3-3

| Tumor | Test Substance | Daily Dose | Average Survival Days (%) |
|---|---|---|---|
| Mouse Sarcoma 180 | $CB_{X3}^{*(1)}$ | 1 unit/kg | 110 |
| | | 3 unit/kg | 129 |
| | | 10 unit/kg | 157 |
| | $CB_{X3}^{*(2)}$ | 1 unit/kg | 108 |
| | | 3 unit/kg | 131 |
| | | 10 unit/kg | 150 |
| | Mitomycin C | 0.5 mg/kg | 142 |
| Ehrlich Ascites Tumor | $CB_{X3}^{*(1)}$ | 1 unit/kg | 139 |
| | | 3 unit/kg | 155 |
| | | 10 unit/kg | 181 |
| | $CB_{X3}^{*(2)}$ | 1 unit/kg | 132 |
| | | 3 unit/kg | 157 |
| | | 10 unit/kg | 179 |
| | Mitomycin C | 0.5 mg/kg | 166 |

(Notes)
*(1)$CB_{X3}$ obtained in Example 26
*(2)$CB_{X3}$ obtained in Example 29

As clearly seen in the results above, CB showed a significant anti-tumor effect on mice to which both Sarcoma 180 and Enrlich tumor had been transplanted, respectively.

Experiment 3: Influence on the Survival Days of Leukemic Mice $BDF_1$-strain male mice weighing 20–25 g were intraperitoneally transplanted with $10^5$ cells per animal of mouse leukemia L1210 or $10^6$ cells per animal of mouse leukemia P338, and the period of survival in days was observed. $CB_X$ obtained in example 10, $CB_{X1}$ obtained in Example 16, $CB_{X2}$ obtained in Example 20 and $CB_{X3}$ obtained in Example 26 or 29 were intraperitoneally administered to groups of 5 mice, either daily from one day after the transplantation until death (for $CB_X$, $CB_{X1}$ and $CB_{X2}$) or once on the day following the transplantation (for $CB_{X3}$). The results are expressed in percentages of the average survival days to that of the control group and set forth in Tables 4-1 to 4-3.

TABLE 4-1

| Tumor | Test Substance | Daily Dose | Average Survival Days (%) |
|---|---|---|---|
| Mouse Leukemia L1210 | $CB_X$ | 0.4 unit/kg | 105 |
| | | 1.2 unit/kg | 123 |
| | | 4 unit/kg | 151 |
| | Mitomycin C | 0.5 mg/kg | 128 |
| | Cyclophosphamide | 20 mg/kg | 172 |
| Mouse Leukemia P388 | $CB_X$ | 0.4 unit/kg | 113 |
| | | 1.2 unit/kg | 128 |
| | | 4 unit/kg | 144 |
| | Mitomycin C | 0.5 mg/kg | 133 |
| | Cyclophosphamide | 20 mg/kg | 147 |

TABLE 4-2

| Tumor | Test Substance | Daily Dose | Average Survival Days (%) |
|---|---|---|---|
| Mouse Leukemia L1210 | $CB_{X1}$ | 3 unit/kg | 108 |
| | | 10 unit/kg | 122 |
| | | 30 unit/kg | 149 |
| | $CB_{X2}$ | 1 unit/kg | 110 |
| | | 3 unit/kg | 121 |
| | | 10 unit/kg | 151 |
| | Mitomycin C | 0.5 mg/kg | 136 |
| | Cyclophosphamide | 20 mg/kg | 149 |
| Mouse Leukemia P338 | $CB_{X1}$ | 1 unit/kg | 110 |
| | | 3 unit/kg | 126 |
| | | 10 unit/kg | 147 |
| | $CB_{X2}$ | 0.3 unit/kg | 109 |

TABLE 4-2-continued

| Tumor | Test Substance | Daily Dose | Average Survival Days (%) |
|---|---|---|---|
| | | 1 unit/kg | 125 |
| | | 3 unit/kg | 151 |
| | Mitomycin C | 0.5 mg/kg | 130 |
| | Cyclophosphamide | 20 mg/kg | 145 |

TABLE 4-3

| Tumor | Test Substance | Daily Dose | Average Survival Days (%) |
|---|---|---|---|
| Mouse Leukemia L1210 | $CB_{X3}$*[1] | 10 unit/kg | 109 |
| | | 30 unit/kg | 120 |
| | | 100 unit/kg | 149 |
| | $CB_{X3}$*[2] | 10 unit/kg | 111 |
| | | 30 unit/kg | 121 |
| | | 100 unit/kg | 146 |
| | Mitomycin C | 5.0 mg/kg | 132 |
| Mouse Leukemia P388 | $CB_{X3}$*[1] | 10 unit/kg | 122 |
| | | 30 unit/kg | 145 |
| | | 100 unit/kg | 176 |
| | $CB_{X3}$*[2] | 10 unit/kg | 120 |
| | | 30 unit/kg | 148 |
| | | 100 unit/kg | 171 |
| | Mitomycin C | 5.0 mg/kg | 141 |

(Notes)
*[1] $CB_{X3}$ obtained in Example 26
*[2] $CB_{X3}$ obtained in Example 29

As clearly seen in results above, CB showed a significant anti-tumor effect on both tumor-bearing mice with mouse leukemia L1210 and P388, respectively.

Experiment 4: Influence on the Survival Days of Lung Carcinoma bearing Mice $BDF_1$-strain male mice weighing 20–25 g were transplanted with $2 \times 10^6$ cells of Lewis's lung carcinoma intramuscularly to the right thigh, and the survival days were observed. $CB_X$ obtained in example 7, $CB_{X1}$ obtained in Example 17, $CB_{X2}$ obtained in Example 22 and $CB_{X3}$ obtained in Example 26 or 29 were intravenously administered to groups of 6 mice daily from one day after the transplantation until death. The results are expressed in percentages of the average survival days to that of the control group and set forth in Tables 5-1 to 5-2.

TABLE 5-1

| Test Substance | Daily Dose | Average Survival Days (%) |
|---|---|---|
| $CB_X$ | 1.2 unit/kg | 104 |
| | 4 unit/kg | 112 |
| | 12 unit/kg | 146 |
| Mitomycin C | 0.5 mg/kg | 121 |
| Cyclophosphamide | 20 mg/kg | 163 |

TABLE 5-2

| Test Substance | Daily Dose | Average Survival Days (%) |
|---|---|---|
| $CB_{X1}$ | 1 unit/kg | 107 |
| | 3 unit/kg | 113 |
| | 10 unit/kg | 145 |
| $CB_{X2}$ | 1 unit/kg | 109 |
| | 3 unit/kg | 121 |
| | 10 unit/kg | 143 |
| $CB_{X3}$*[1] | 1 unit/kg | 115 |
| | 3 unit/kg | 143 |
| | 10 unit/kg | 157 |

TABLE 5-2-continued

| Test Substance | Daily Dose | Average Survival Days (%) |
|---|---|---|
| $CB_{X3}$*[2] | 1 unit/kg | 111 |
| | 3 unit/kg | 136 |
| | 10 unit/kg | 159 |
| Mitomycin C | 0.5 mg/kg | 120 |
| Cyclophosphamide | 20 mg/kg | 164 |

(Notes)
*[1] $CB_{X3}$ obtained in Example 26
*[2] $CB_{X3}$ obtained in Example 29

Experiment 5: Influence on the Survival Period in Days of Melanoma bearing Mice $BDF_1$-strain male mice weighing 20–25 g had transplanted subcutaneously in their back $10^6$ cells per animal of mouse melanoma B 16, and the survival days were observed. $CB_X$ obtained in example 10 and $CB_{X3}$ obtained in Example 26 or 29 were intravenously administered to groups of 7 mice daily from one day after the transplantation until death. The results are expressed in percentages of the average survival days of the control group and set forth in Tables 6-1 to 6-2.

TABLE 6-1

| Test Substance | Daily Dose | Average Survival Days (%) |
|---|---|---|
| $CB_X$ | 1.2 unit/kg | 112 |
| | 4 unit/kg | 135 |
| | 12 unit/kg | 180 |
| Mitomycin C | 0.5 mg/kg | 138 |
| Cyclophosphamide | 20 mg/kg | 158 |

TABLE 6-2

| Test Substance | Daily Dose | Average Survival Days (%) |
|---|---|---|
| $CB_{X3}$*[1] | 1 unit/kg | 110 |
| | 3 unit/kg | 131 |
| | 10 unit/kg | 178 |
| $CB_{X3}$*[2] | 1 unit/kg | 116 |
| | 3 unit/kg | 129 |
| | 10 unit/kg | 176 |
| Mitomycin C | 0.5 mg/kg | 140 |

(Notes)
*[1] $CB_{X3}$ obtained in Example 26
*[2] $CB_{X3}$ obtained in Example 29

As clearly seen in the results above, CB evidently showed an anti-tumor effect on the mice bearing mouse melanoma B 16.

Experiment 6: Influence on the Lung Metastasis of Cancer

Groups of $BDF_1$-strain male mice weighing 20–30 g, 6 animals in each group, had transplanted subcutaneously into their backs 2 mm square segments of Lewis's lung cancer. $CB_X$ obtained in Example 6, $CB_{X1}$ obtained in Example 15, $CB_{X2}$ obtained in Example 20 and CBF obtained were administered intravenously once a day for 12 days from the 9th day after transplantation. On the 21st day after transplantation, the mass of primary tumor was isolated and weighed, and the number of the metastasized nodes in the animal's lungs was calculated according to the method of Wexler, H. (J. Natl. Cancer Institute, Vol. 36 641 (1966)). The results are set forth in Tables 7-1 to 7-2.

TABLE 7-1

| Experiment | Test substance | Daily Dose | Tumor Weight (g) | No. of Metastasized Nodes in Lung |
|---|---|---|---|---|
| 1 | Control | | 9.6 ± 1.9 | 29.2 ± 7.3 |
|   | $CB_X$ | 4 unit/kg | 5.1 ± 1.6* | 6.8 ± 3.2* |
|   |       | 40 unit/kg | 3.0 ± 0.3** | 0.4 ± 0.4** |
|   | Cyclophosphamide | 20 unit/kg | 3.4 ± 0.7** | 0.4 ± 0.2** |
| 2 | Control | | 7.3 ± 0.3 | 29.2 ± 1.4 |
|   | $CB_X$ | 4 unit/kg | 4.1 ± 1.2* | 6.7 ± 2.1* |
|   |       | 40 unit/kg | 2.3 ± 0.2** | 0.5 ± 0.2** |
|   | CBF   | 4 unit/kg | 6.6 ± 0.6 | 22.0 ± 5.0 |
|   |       | 40 unit/kg | 4.2 ± 0.4* | 21.4 ± 4.5 |

TABLE 7-2

| Test substance | Daily Dose | Tumor Weight (g) | No. of Metastasized Nodes in Lung |
|---|---|---|---|
| Control | | 7.8 ± 0.5 | 29.6 ± 1. |
| $CB_{X1}$ | 3 unit/kg | 4.3 ± 1.3* | 7.3 ± 2.0* |
|           | 30 unit/kg | 2.4 ± 0.3** | 0.5 ± 0.3** |
| $CB_{X2}$ | 3 unit/kg | 4.9 ± 1.3* | 7.1 ± 1.9* |
|           | 30 unit/kg | 2.1 ± 0.5** | 0.7 ± 0.3** |
| CBF | 3 unit/kg | 6.8 ± 0.6 | 23.0 ± 5.2 |
|     | 30 unit/kg | 4.3 ± 0.5* | 22.4 ± 4.4 |
| Cyclophosphamide | 20 unit/kg | 3.5 ± 0.6** | 0.6 ± 0.3** |

(Notes)
The results in the tables are expressed as (average) ± (standard error)
*Statistically different from the control group at a significance level of $p \leq 5\%$.
**Statistically different from the control group at a significance level of $p \leq 1\%$.

As clearly seen in the results above, $CB_X$ very successfully suppressed the primary lung cancer and its lung metastases, whereas CBF had almost no effect on the lung metastases.

Experiment 7: Effect on Inducing Differentiation of Tumor Cells

According to the method of Hozumi, M. et al (Cancer Research, Vol, 40, 2919–2924 (1980)), $5 \times 10^5$ cells of acute myelogenous leukemia cells M-1 (supplied from Dr. Motoo Hozumi, Saitama Cancer Center) were suspended in 1 ml of Eagle's medium containing 10% calf serum and also containing amino acids and vitamins in amounts twice the ordinary levels, to which each test substance had been added, and cultured at 37° C. for 48 hours in a 5% $CO_2$, 95% air atmosphere. Thereafter, the cells were resuspended in a medium containing 0.2% polystyrene latex particles (Dow Chemical Co.) and incubated at 37° C. for 4 hours. Then the total number of cells which phagocytotized the particles and the total number of cells were counted under a light microscope, and the differentiation rate was calculated from the ratio of these cells. The results are set forth in Table 8.

TABLE 8

| Test Substance | Concentration | Differentiation Rate (%) |
|---|---|---|
| Control | | 1 |
| $CB_X$ | 0.004 unit/ml | 8 |
|        | 0.04 unit/ml | 11 |
|        | 0.4 unit/ml | 18 |
| Dexamethasone | 20.0 ng/ml | 25 |

$CB_X$ exhibited the effect on inducing differentiation.

Experiment 8: Pyrogen Test

According to the method described in the Japanese Pharmacopeia, $CB_X$ obtained in Example 3 was intravenously administered to white rabbits at a dose of 100 units per animal. The results of measurement of the rectal temperature up to 3 hours later using a thermocouple type thermometer are set forth in Table 9.

TABLE 9

| Rabbit | Weight (kg) | Rectal Temperature pre- and post-$CB_X$ Injection (°C.) | | | |
|---|---|---|---|---|---|
|   |   | Before Injection | 1 hour Later | 2 hours Later | 3 hours Later |
| A | 2.0 | 38.90 | 38.70 | 38.80 | 38.80 |
| B | 2.0 | 38.90 | 38.90 | 38.97 | 38.97 |
| C | 2.0 | 39.25 | 39.25 | 39.22 | 39.30 |

Experiment 9: Influence on Breast Cancer bearing Mice

BALB/C strain nude mice weighing 20–25 g, 6 animals in each group, had transplanted subcutaneously into their backs 2 mm square segments of human breast cancer MX-1. $CB_{X3}$ obtained in Example 26 or 29 was intravenously administered into the mice for 14 days from the 14th day after the transplantation. On the 15th day after the first administration, the volume of the primary tumor was measured. The results are set forth in Table 10.

TABLE 10

| Test substance | Daily Dose | Tumor Volume*[1] ($cm^3$) |
|---|---|---|
| Control | | 9.7 ± 2.2 |
| $CB_{X3}$*[2] | 1 unit/kg | 7.6 ± 1.3 |
|              | 3 unit/kg | 4.3 ± 1.3* |
|              | 10 unit/kg | 2.2 ± 0.9** |
| $CB_{X3}$*[3] | 1 unit/kg | 7.3 ± 1.2 |
|              | 3 unit/kg | 4.6 ± 1.4* |
|              | 10 unit/kg | 2.0 ± 1.0** |
| Mitomycin C | 0.5 mg/kg | 4.4 ± 1.1* |

(Notes)
*[1](Average Value) ± (Standard Error)
*[2]$CB_{X3}$ obtained in Example 26
*[3]$CB_{X3}$ obtained in Example 29
*Statistically different from the control group at a significance level of $p \leq 5\%$.
**Statistically different from the control group at a significance level of $p \leq 1\%$.

Experiment 10: Influence on Methylcholanthrene-Induced Tumor

3-Methylcholanthrene dissolved in olive oil was subcutaneously injected to the lateral abdomen of ddY-strain mice, weighing 20–25 g, 8 animals in each group, at 0.5 mg per mouse. $CB_{X3}$ obtained in Example 26 or 29 was intravenously administered to the mice once a day for 21 days from about 60 days after the 3-Methylcholanthrene injection. On the 21st day after the first $CB_{X3}$ administration, the volume of the tumor was measured. The results are set forth in Table 11.

TABLE 11

| Test Substance | Daily Dose | Tumor Volume*[1] ($cm^3$) |
|---|---|---|
| Control | | 10.5 ± 2.3 |
| $CB_{X3}$*[2] | 1 unit/kg | 8.5 ± 1.4 |
|              | 3 unit/kg | 5.4 ± 1.4* |
|              | 10 unit/kg | 2.5 ± 0.7** |
| $CB_{X3}$*[3] | 1 unit/kg | 8.9 ± 1.5 |
|              | 3 unit/kg | 5.1 ± 1.3* |
|              | 10 unit/kg | 2.2 ± 0.8** |

TABLE 11-continued

| Test Substance | Daily Dose | Tumor Volume*[1] (cm³) |
|---|---|---|
| Mitomycin C | 0.5 mg/kg | 6.6 ± 1.3* |

(Notes)
*[1](Average Value) ± (Standard Error)
*[2]$CB_{X3}$ obtained in Example 26
*[3]$CB_{X3}$ obtained in Example 29
*Statistically different from the control group at a signifcance level of p ≦ 5%.
**Statistically different from the control group at a significance level of p ≦ 1%.

As clear from the above results, $CB_{X3}$ evidently shows an anti-tumor effect on spontaneous tumors.

Experiment 11: Toxicity Test (Single Administration)

$BDF_1$-strain male mice weighing 20–25 g, 10 animals in each group, were intravenously administered the CB and the number of dead animals was observed for 7 days. As a result, all 10 animals survived without showing any change in body weight and general conditions, even when administered 10,000 unit/kg of $CB_X$, $CB_{X1}$, or $CB_{X2}$ or 100,000 unit/kg of $CB_{X3}$.

Experiment 12: Toxicity Test (30-Day Continuous Administration)

$BDF_1$-strain male mice weighing 20–25 g, 10 animals in each group, were intravenously administered the CB for 30 days, and the number of dead animals, the change in body weight and the general conditions were observed. The body weight was weighed between 9 a.m. and 10 a.m., and the observation of the general conditions was conducted on the 10th, 20th and 30th days according to the method of Arvien (Science, Vol. 36, 123 (1962)). As a result, there was no dead animal in these 30 days when 1,000 unit/kg/day of $CB_X$, $CB_{X1}$ or $CB_{X2}$, or 10,000 unit/kg/day of $CB_{X3}$ was administered, and the weight gain curve was more or less the same as that of the control group. Further, the general conditions were found to be normal as in the control group.

As can be seen in the experiments described above, CB selectively suppresses the growth of tumor cells, and moreover, it not only remarkably suppresses the cancer metastasis but also is extremely effective against various tumors and is still very safe even at doses higher than the dose at which the pharmaceutical effect would be manifest. Therefore, CB is extremely useful for therapy of various tumors such as stomach cancer, lung cancer, hepatoma, colon cancer, breast cancer, uterus cancer, leukemia, etc.

CB may be administered in the form of conventional preparations, such as injections, eye drops, nasal drops, inhalants, topical preparations, oral preparations, rectal preparations, vaginal preparations etc. The daily therapeutic dose of CB for an adult is not particularly restricted because of the high safety thereof, but generally it is 0.5–500,000 units, preferably 0.5–5,000 units for topical application, 20–100,000 units for systemic administration, such as intravenous injection, intramuscular injection etc., and 50–500,000 units for oral administration. The dose may be suitably adjusted depending on the method of use or the severity of the diseases. The preparation may contain each of $CB_X$, $CB_{X1}$, $CB_{X2}$ and $CB_{X3}$ alone or in combination with each other in any desired ratio.

CB may be formulated into pharmaceutical preparations by any conventional method using pharmaceutically acceptable carriers, bases, excipients, etc. Preferably, it is employed as an oral preparation such as an enteric preparation, e.g. capsules, tablets, powder, etc.; a rectal preparation such as a rectal suppository, an injection such as an aqueous injection, or reconstitutable preparation of lyophilized powder for dissolution in distilled water for injection before use; and a topical preparation such as an ointment, lotion etc. In addition, it may be used as eye drops, nasal drops, or inhalants.

Examples of solid carriers and excipients usable advantageously herein include common excipients such as lactose, mannitol, corn starch and potato starch; binders such as crystalline cellulose, cellulose derivatives, arabic gum, corn starch and gelatin; disintegrators such as corn starch, potato starch and calcium carbohydroxymethylcellulose; and lubricants such as talc and magnesium stearate. Examples of liquid carriers usable advantageously herein include distilled water for injection, physiological saline solution, vegetable oils for injection and glycols such as propylene glycol and polyethylene glycol.

Examples are given below, but this invention is not intended to be restricted thereto.

EXAMPLE 1

Human lymphocytes ($2 \times 10^{10}$ cells) were suspended in 4,000 ml of Eagle's medium containing 10% calf serum and cultured at 37° C. for 48 hours in a 5% $CO_2$, 95% air atmosphere. Thereafter, the supernatant of the culture medium was dialyzed against 0.01M phosphate buffer (pH 7.2), and a fraction salted out with 40–80% ammonium sulfate was obtained from the dialyzate. This fraction was redialyzed against said phosphate buffer and then subjected to gel filtration using Sephadex G-100 (Pharmacia Co.). A fraction of a molecular weight of 12,000–17,000 was collected, which was designated as the crude $CB_X$ fraction, while the earlier eluted fraction was designated as the crude CBF fraction. The crude $CB_X$ fraction was adsorbed on Ulex europeus agglutinin (Maruzen Oil Co.)-conjugated Sephadex, eluted with 0.01M phosphate buffer containing 0.5M fucose. After removing fucose by dialysis, $CB_X$ was adsorbed again on the Ulex europeus agglutinin-conjugated Sephadex, followed by elution by gradient method using phosphate buffer (pH 7.2), whereby purified $CB_X$ was eluted. A total of 0.02 mg of $CB_X$ was obtained. The total activity of the obtained $CB_X$ was 150 units as determined by the above described method. Thus the specific activity of the purified $CB_X$ was 7,500 unit/mg.

EXAMPLE 2

Bovine lymphocytes ($2 \times 10^9$ cells) were suspended in 1,000 ml of Eagle's medium containing 10% calf serum and cultured at 37° C. for 48 hours in a 5% $CO_2$, 95% air atmosphere. Thereafter, the supernatant of the culture medium was subjected to the procedures in Example 1 for purification of $CB_X$ and 0.01 mg of $CB_X$ was obtained. The total activity of the obtained $CB_X$ was 20 units thus the specific activity of the purified $CB_X$ was 2,000 unit/mg.

EXAMPLE 3

Mouse lymphocytes ($5 \times 10^{10}$ cells) were suspended in 5,000 ml of Eagle's medium containing 10% calf serum, and cultured at 37° C. for 48 hours in a 5% $CO_2$, 95% air atmosphere. Thereafter, the supernatant of culture medium was subjected to the procedures in Example 1 for purification of $CB_X$, and 0.12 mg of $CB_X$ was obtained. The total activity of the obtained $CB_X$ was 400 units, thus the specific activity of the purified $CB_X$ was 3,333 unit/mg.

EXAMPLE 4

BALL-1 cells (human cell line, $1 \times 10^{10}$ cells), which had been precultured, were suspended in 2,000 ml of Eagle's medium containing 10% calf serum, and cultured at 37° C. for 48 hours in a 5% $CO_2$, 95% air atmosphere. Thereafter, the supernatant of the culture medium was subjected to the procedures in Example 1 for purification of $CB_X$, and 0.7 mg of $CB_X$ was obtained. The total activity of the obtained $CB_X$ was 4,000 units, thus the specific activity of the purified $CB_X$ was 5,714 unit/mg.

EXAMPLE 5

Flow 7000 cells (human fibroblasts line, $3 \times 10^9$ cells), which had been grown by cell culture, were suspended in 600 ml of Eagle's medium containing 10% calf serum, and cultured at 37° C. for 48 hours in a 5% $CO_2$, 95% air atmosphere. Thereafter, the supernatant of the culture medium was subjected to the procedures in Example 1 for purification of $CB_X$, and 0.005 mg of $CB_X$ was obtained. The total activity of the obtained $CB_X$ was 10 units, thus the specific activity of the purified $CB_X$ was 2,000 unit/mg.

EXAMPLE 6

Human lymphocytes ($2 \times 10^{10}$ cells) were suspended in 4,000 ml of Eagle's medium containing 10% calf serum, and after adding phytohemagglutinin (Difco Co.) at a final concentration of 50 $\mu$g/ml, cultured at 37° C. for 48 hours in a 5% $CO_2$, 95% air atmosphere. Thereafter, the supernatant of the culture medium was subjected to the procedures in Example 1 for purification of $CB_X$, and 1.0 mg of $CB_X$ was obtained. The total activity of the obtained $CB_X$ was 10,000 units, thus the specific activity of the purified $CB_X$ was 10,000 unit/mg.

EXAMPLE 7

Flow 7000 cells human fibroblasts line, $3 \times 10^9$ cells) were suspended in 600 ml of Eagle's medium containing 10% calf serum, and after adding phytohemagglutinin at a final concentration of 50 $\mu$g/ml, cultured at 37° C. for 48 hours in a 5% $CO_2$, 95% air atmosphere. Thereafter, the supernatant of the culture medium was subjected to the procedures in Example 1 for purification of $CB_X$, and 60 $\mu$g of $CB_X$ was obtained. The total activity of the obtained $CB_X$ was 480 units, thus the specific activity of the purified $CB_X$ was 8,000 unit/mg.

EXAMPLE 8

TALL-1 cells (human cell line, $9 \times 10^9$), which had been grown by cell culture, were suspended in 800 ml of Eagle's medium containing 10% calf serum, and after adding phytohemagglutinin at a final concentration of 50 $\mu$g/ml, cultured at 37° C. for 48 hours in a 5% $CO_2$, 95% air atmosphere. Thereafter, the supernatant of the culture medium was subjected to the procedures in Example 1 for purification of $CB_X$, and 0.8 mg of $CB_X$ was obtained. The total activity of the obtained $CB_X$ was 7,500 units, thus the specific activity of the purified $CB_X$ was 9,375 unit/mg.

EXAMPLE 9

Adult mice were pre-treated by irradiating with X-ray of about 400 REM to suppress their immune responses, and then TALL-1 cells (human origin) were transplanted into them subcutaneously. Thereafter, the mice were fed for 3 weeks. The mass of tumor that subcutaneously formed weighing about 10 g was isolated, minced and dissociated in a physiological saline solution containing trypsin, then the dispersed cells were collected. These cells were treated according to the method in Example 1 to obtain $CB_X$. The yield of $CB_X$ was about 190 units per mouse.

EXAMPLE 10

BALL-1 cells (human cell line, $9 \times 10^9$ cells) were suspended in 1,800 ml of Eagle's medium containing 10% calf serum, and, after adding $9 \times 10^6$ pfu (plaque forming units) of Sendai virus (HVJ), cultured at 37° C. for 48 hours in a 5% $CO_2$, 95% air atmosphere. Thereafter, the supernatant of the culture medium was subjected to the procedures in Example 1 for purification of $CB_X$, and 720 $\mu$g of $CB_X$ was obtained. The total activity of the obtained $CB_X$ was 7,920 units, thus the specific activity of the purified $CB_X$ was 11,000 unit/mg.

$CB_X$ obtained above was dissolved in physiological saline at a concentration of 1 mg/ml, and optical rotation of the solution at 598 nm (Na. D line) was measured at 26.5°–28.5° C. by a polarimeter (Nihon Bunko DIP-181) using a microcell of 10 mm in light path. The optical rotation of physiological saline as a control was assured to be zero. $CB_X$ showed levo-rotation.

$CB_X$ (10 $\mu$g) obtained above was prepared into a microtablet with potassium bromide powder to measure IR spectrum of $CB_X$. The integrated measurement (60 times) was carried out by Fourier transform infrared spectrophotometer fX-6201 (Analect Instruments Co.). The result is shown in FIG. 1.

EXAMPLE 11

BALL-1 cells (human origin) were transplanted subcutaneously into adult nude mice which were then fed for 3 weeks. The resultant mass of tumor that formed subcutaneously weighing about 10 g each was isolated, minced, and then dissociated in a physiological saline solution containing trypsin, after which the dispersed cells were collected. These cells were washed with Eagle's medium containing 5% human serum, then $2 \times 10^9$ cells thereof were suspended in 2,000 ml of the same medium and cultured at 37° C. for 48 hours in a 5% $CO_2$, 95% air atmosphere. Thereafter, the supernatant of the culture medium was subjected to the procedures in Example 1 to obtain $CB_X$. The yield of $CB_X$ was about 200 units per nude mouse.

EXAMPLE 12

JBL cells (human cell line) were suspended in physiological saline, and the suspension was then placed in a plastic cylindrical diffusion chamber having a capacity of about 10 ml and fitted with a membrane filter having a pore size of about 0.5 microns, and this chamber was placed in the peritoneal cavity of an adult rat. The rat was fed for 4 weeks, and the chamber was removed therefrom.

The cell concentration of the human cells thus obtained was found to be about $5 \times 10^9$ cells per ml, which represents about $10^3$ fold or more times the concentrations obtained by culturation in vitro in a nutrient medium in a 5% $CO_2$, 95% air atmosphere.

A total of $1 \times 10^{10}$ JBL cells obtained by the method described above were suspended in 4,000 ml of Eagle's medium containing 10% calf serum, and cultured at 37°

C. for 48 hours in a 5% $CO_2$, 95% air atmosphere. Thereafter, the supernatant of the culture medium was subjected to the procedures in Example 1 to obtain $CB_X$. The yield of $CB_X$ was about 350 units per rat.

EXAMPLE 13

BALL-1 cells (human origin) were transplanted subcutaneously into adult nude mice, which were then fed for 5 weeks. Thereafter, each mouse was intraperitoneally injected with 1 mg of phytohemagglutinin, and sacrificed 24 hours after the injection, and ascites was collected. The ascites were centrifuged at 4° C. and 1,000 g, and the obtained supernatant was dialyzed against a physiological saline solution containing 0.01M phosphate buffer (pH 7.2) for 15 hours. The solution was further ultrafiltered with a membrane filter and the filtrate was concentrated to obtain a solution containing $CB_X$. The amount of $CB_X$ was about 8,000 units per nude mouse.

EXAMPLE 14

NALL-1 cells (human cell line) were suspended in physiological saline and poured into a plastic cylindrical diffusion chamber having a capacity of about 10 ml and fitted with a membrane filter with a pore size of about 0.5 microns, and this chamber was placed in the peritoneal cavity of an adult rat. This rat was fed for 4 weeks, and then the chamber was removed. The cells thus grown were washed with Eagle's medium containing 5% human serum, and resuspended in the same medium at a cell concentration of about $5 \times 10^6$ cells per ml. The suspension was supplemented with about 200 µg/ml of phytohemagglutinin, and the mixture was incubated at 37° C. for 2 days to induce the production of $CB_X$. $CB_X$ thus produced was purified and concentrated as described in Example 1, and it was further lyophilized to obtain a powder of $CB_X$. The yield of $CB_X$ was about 15,000 units per rat.

EXAMPLE 15

According to the procedures described in Example 6, human lymphocytes were cultured, and the supernatant of the culture medium was subjected to purification to obtain a purified fraction with a molecular weight of 70,000–90,000. This fraction was designated as the $CB_{X1}$. The total activity of the 0.1 mg of purified $CB_{X1}$ was 5,000 units, thus the specific activity of the purified $CB_{X1}$ was 50,000 unit/mg.

Optical rotation of $CB_{X1}$ obtained above was measured as described in Example 10. $CB_{X1}$ showed dextrorotation.

Figure 2:
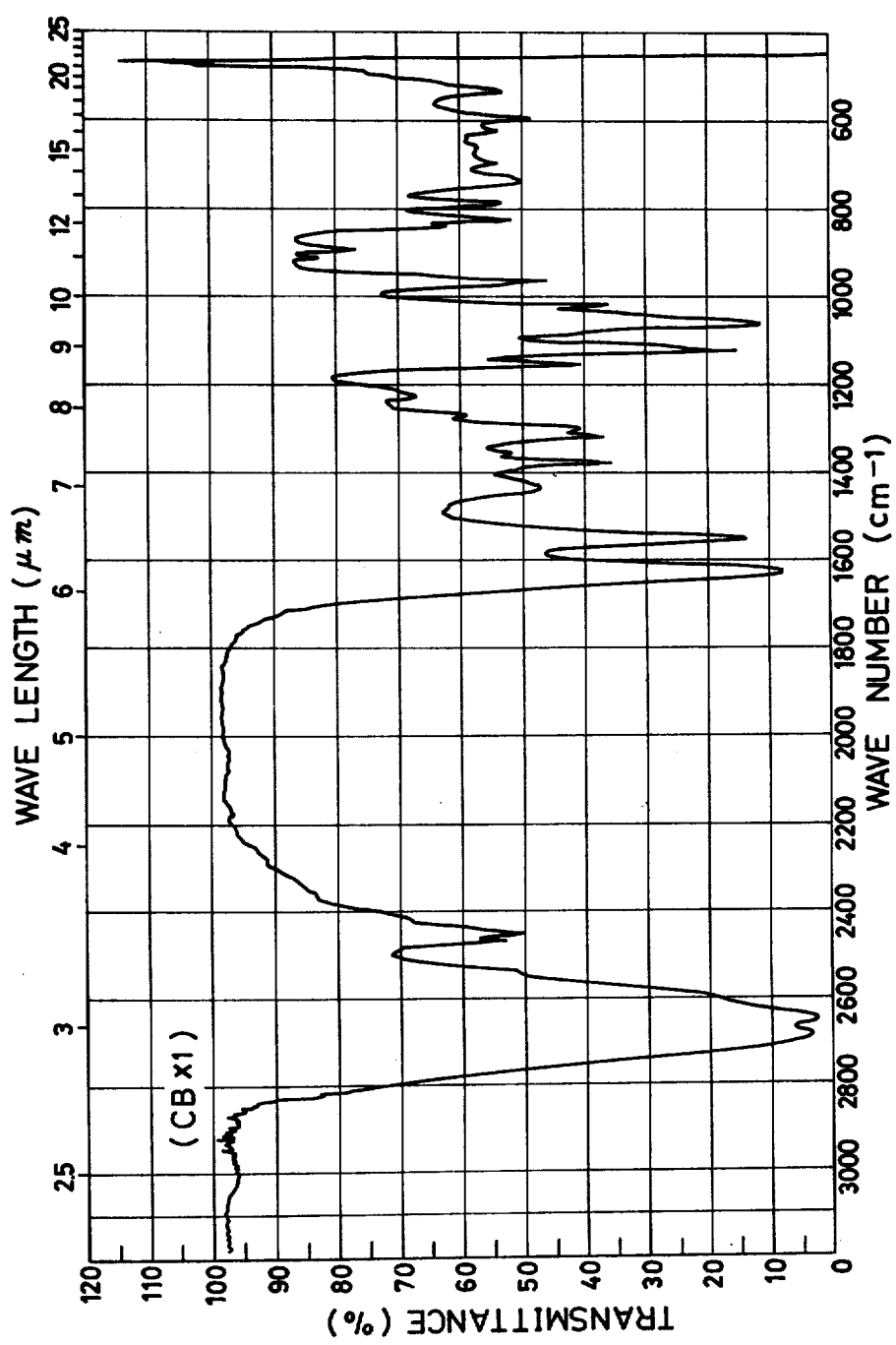
FIG. 2 shows the IR spectrum of $CB_{X1}$ measured in Example 15.

IR measurement of $CB_{X1}$ obtained above was carried out as described in Example 10. The result is shown in FIG. 2.

EXAMPLE 16

According to the procedures described in Example 10, BALL-1 cells were cultured, and the supernatant of the culture medium was subjected to purification to obtain a purified $CB_{X1}$. The total activity of the 100 µg of purified $CB_{X1}$ obtained was 4,200 units, thus the specific activity of the purified $CB_{X1}$ was 42,000 unit/mg.

EXAMPLE 17

According to the procedures described in Example 7, Flow 7000 cells were cultured, and the supernatant of the culture medium was subjected to purification to obtain purified 10 µg of $CB_{X1}$. The total activity of the obtained $CB_{X1}$ was 250 units, thus the specific activity of the purified $CB_{X1}$ was 25,000 unit/mg.

EXAMPLE 18

According to the procedures described in Example 2, bovine lymphocytes were cultured, and the supernatant of the culture medium was subjected to purification to obtain 0.002 mg of purified $CB_{X1}$. The total activity of the obtained $CB_{X1}$ was 14 units, thus the specific activity of the purified $CB_{X1}$ was 7,000 unit/mg.

EXAMPLE 19

According to the procedures described in Example 4, BALL-1 cells were cultured, and the supernatant of the culture medium was subjected to purification to obtain 0.2 mg of purified $CB_{X1}$. The total activity of the obtained $CB_{X1}$ was 2,300 units, thus the specific activity of the purified $CB_{X1}$ was 11,500 unit/mg.

EXAMPLE 20

According to the procedures described in Example 6, human lymphocytes were cultured, and the supernatant of the culture medium was subjected to purification to obtain a purified fraction with a molecular weight of 40,000–50,000. This fraction was designated as the $CB_{X2}$. The total activity of the 0.25 mg of purified $CB_{X2}$ obtained was 5,200 units, thus the specific activity of the purified $CB_{X2}$ was 20,800 unit/mg.

EXAMPLE 21

According to the procedures described in Example 10, BALL-1 cells were cultured, and the supernatant of the culture medium was subjected to purification to obtain 75 µg of purified $CB_{X2}$. The total activity of the obtained $CB_{X2}$ was 10,000 units, thus the specific activity of the purified $CB_{X2}$ was 133,333 unit/mg.

Optical rotation of $CB_{X2}$ obtained above was measured as described in Example 10. $CB_{X2}$ showed dextrorotation.

Figure 3:
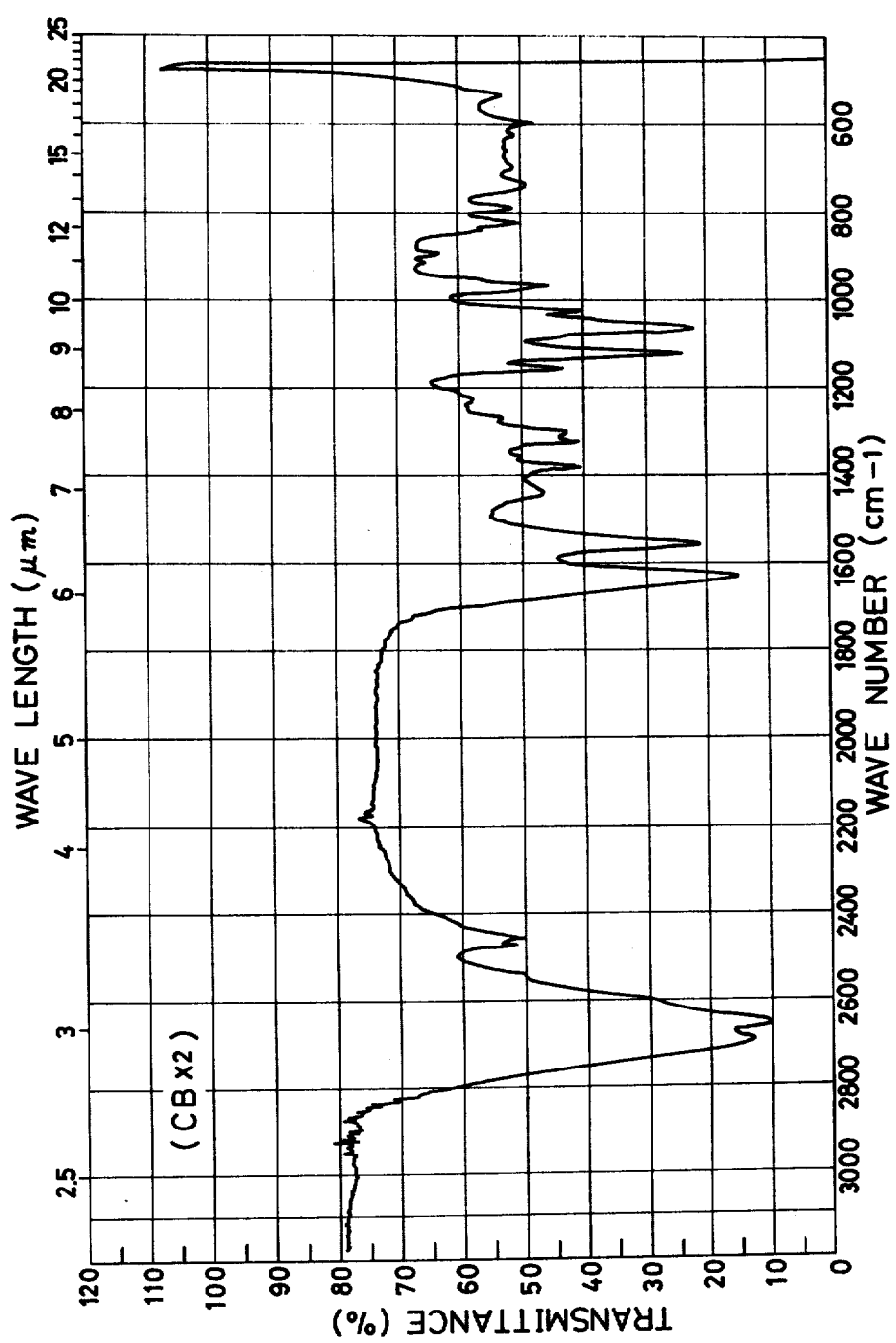
FIG. 3 shows the IR spectrum of $CB_{X2}$ measured in Example 21.

IR measurement of $CB_{X2}$ obtained above was carried out as described in Example 10. The result is shown in FIG. 3.

EXAMPLE 22

According to the procedures described in Example 7, Flow 7000 cells were cultured, and the supernatant of the culture medium was subjected to purification to obtain 20 µg of purified $CB_{X2}$. The total activity of the obtained $CB_{X2}$ was 500 units, thus the specific activity of the purified $CB_{X2}$ was 25,000 unit/mg.

EXAMPLE 23

According to the procedures described in Example 2, bovine lymphocytes were cultured, and supernatant of the culture medium was subjected to purification to obtain 0.001 mg of purified $CB_{X2}$. The total activity of the obtained $CB_{X2}$ was 40 units, thus the specific activity of the purified $CB_{X2}$ was 40,000 unit/mg.

EXAMPLE 24

According to the procedures described in Example 4, BALL-1 cells were cultured, and supernatant of the culture medium was subjected to purification to obtain 0.25 mg of purified $CB_{X2}$. The total activity of the obtained $CB_{X2}$ was 2,900 units, thus the specific activity of the purified $CB_{X2}$ was 11,600 unit/mg.

EXAMPLE 25

Human lymphocytes ($2 \times 10^{10}$ cells) were suspended in 4000 ml of Eagle's medium containing 10% calf serum, and after adding phytohemagglutinin at a concentration of 50 μg/ml the suspension was cultured at 37° C. for 48 hours in a 5% $CO_2$, 95% air atmosphere. Thereafter, the supernatant of the culture medium was dialyzed against 0.01M phosphate buffer (pH 7.2), and a fraction which was salted out with 40–80% ammonium sulfate was obtained from the dialyzate. This fraction was dialyzed again against said phosphate buffer and then subjected to gel filtration using Sephadex G-100 to obtain a fraction having a molecular weight of 7,000–9,000, which was designated as the crude $CB_{X3}$ fraction.

The crude $CB_{X3}$ fraction was adsorbed on phytohemagglutinin-conjugated Sephalose, eluted with 0.01M phosphate buffer (pH 7.2) containing 0.5M N-acetyl-D-galactosamine. After removing N-acetyl-D-galactosamine by dialysis, the resultant solution was applied to carboxymethylcellulose equilibrated with 0.05M phosphate buffer (pH 6.4), followed by elution with 0.5M phosphate buffer (pH 6.4) containing 0.5M sodium chloride. Thus, 0.1 mg of $CB_{X3}$ was obtained. The total activity of the obtained $CB_{X3}$ was 5,000 units.

EXAMPLE 26

Newborn hamsters were pre-treated by injection with antiserum prepared from rabbit in a conventional method so as to reduce their immune responses as much as possible, and then had transplanted subcutaneously into them BALL-1 cells. They were then fed for 3 weeks. The mass of tumors that formed subcutaneously and weighing about 15 g was isolated, minced and dissociated in physiological saline. After washing the obtained cells with serum-free Eagle's medium, $1 \times 10^{11}$ cells thereof were suspended in 150 l of Eagle's medium containing 10% calf serum, and, after adding $9 \times 10^6$ pfu of Sendai virus (HVJ), cultured at 37° C. for 48 hours in a 5% $CO_2$, 95% air atmosphere. The supernatant of the culture medium was dialyzed against 0.01M phosphate buffer (pH 7.2) and a fraction which was salted out with 40–80% ammonium sulfate was obtained from the dialyzate. This fraction was dialyzed again against said phosphate buffer and then subjected to gel filtration using Sephadex G-100 obtain a fraction having a molecular weight of 7,000–9,000, which was designated as the crude $CB_{X3}$ fraction. This crude $CB_{X3}$ fraction was adsorbed on concanavalin A-conjugated Sephalose, and eluted with 0.01M phosphate buffer (pH 7.2) containing 0.5M α-methyl-D-mannoside. After removing the α-methyl-D-mannoside by dialysis, the solution was applied to carboxymethylcellulose equilibrated with 0.5M phosphate buffer (pH 6.0), followed by elution with 0.5M phosphate buffer (pH 7.8). The total activity of the 0.2 mg of $CB_{X3}$ obtained was 12,000 units, and its isoelectric point was 6.3–7.8.

EXAMPLE 27

Flow 7000 cells ($3 \times 10^{10}$ cells) were suspended in 1.0 l of Eagle's medium containing 10% calf serum, and, after adding phytohemagglutinin at a final concentration of 50 μg/ml, cultured at 37° C. for 48 hours in a 5% $CO_2$, 95% air atmosphere. The supernatant of the culture medium was subjected to the procedures in Example 26 for purification of $CB_{X3}$, and 0.1 mg of $CB_{X3}$ was obtained. The total activity of the obtained $CB_{X3}$ was 3,100 units.

EXAMPLE 28

Bovine lymphocytes ($5 \times 10^{10}$ cells) were suspended in 10 l of Eagle's medium containing 10% calf serum, and cultured at 37° C. for 48 hours in a 5% $CO_2$, 95% air atmosphere. Thereafter, the supernatant of culture medium was subjected to the procedures in Example 26 for purification of $CB_{X3}$, and 0.1 mg of purified $CB_{X3}$ was obtained. The total activity of the obtained $CB_{X3}$ was 1,700 units.

EXAMPLE 29

BALL-1 ($5 \times 10^{11}$ cells), which had been grown by cell culture, were suspended in 100 l of Eagle's medium containing 10% calf serum, and cultured at 37° C. for 48 hours in a 5% $CO_2$, 95% air atmosphere. Thereafter, the supernatant of culture medium was dialyzed against 0.01M phosphate buffer (pH 7.2), and a fraction which was salted out with 40–80% ammonium sulfate was obtained. This fraction was dialyzed again against said phosphate buffer and then subjected to gel filtration using Sephadex G-100 to obtain a fraction with a molecular weight of 7,000–9,000. This fraction was adsorbed on phytohemagglutinin-conjugated Sephalose, and eluted with 0.01M phosphate buffer (pH 7.2) containing 0.5M N-acetyl-D-galactosamine. After removing the N-acetyl-D-galactosamine by dialysis, the dialyzed solution was applied to carboxymethylcellulose equilibrated with 0.05M Tris buffer (pH 8.0), followed by elution with 0.05M Tris buffer (pH 8.0) containing 0.5M sodium chloride, whereby 0.1 mg of purified $CB_{X3}$ was obtained. The total activity of $CB_{X3}$ obtained was 8,200 units and its isoelectric point was 8.0–9.2.

Optical rotation of $CB_{X3}$ obtained above was measured as described in Example 10. $CB_{X3}$ did not show optical rotation.

Figure 4:
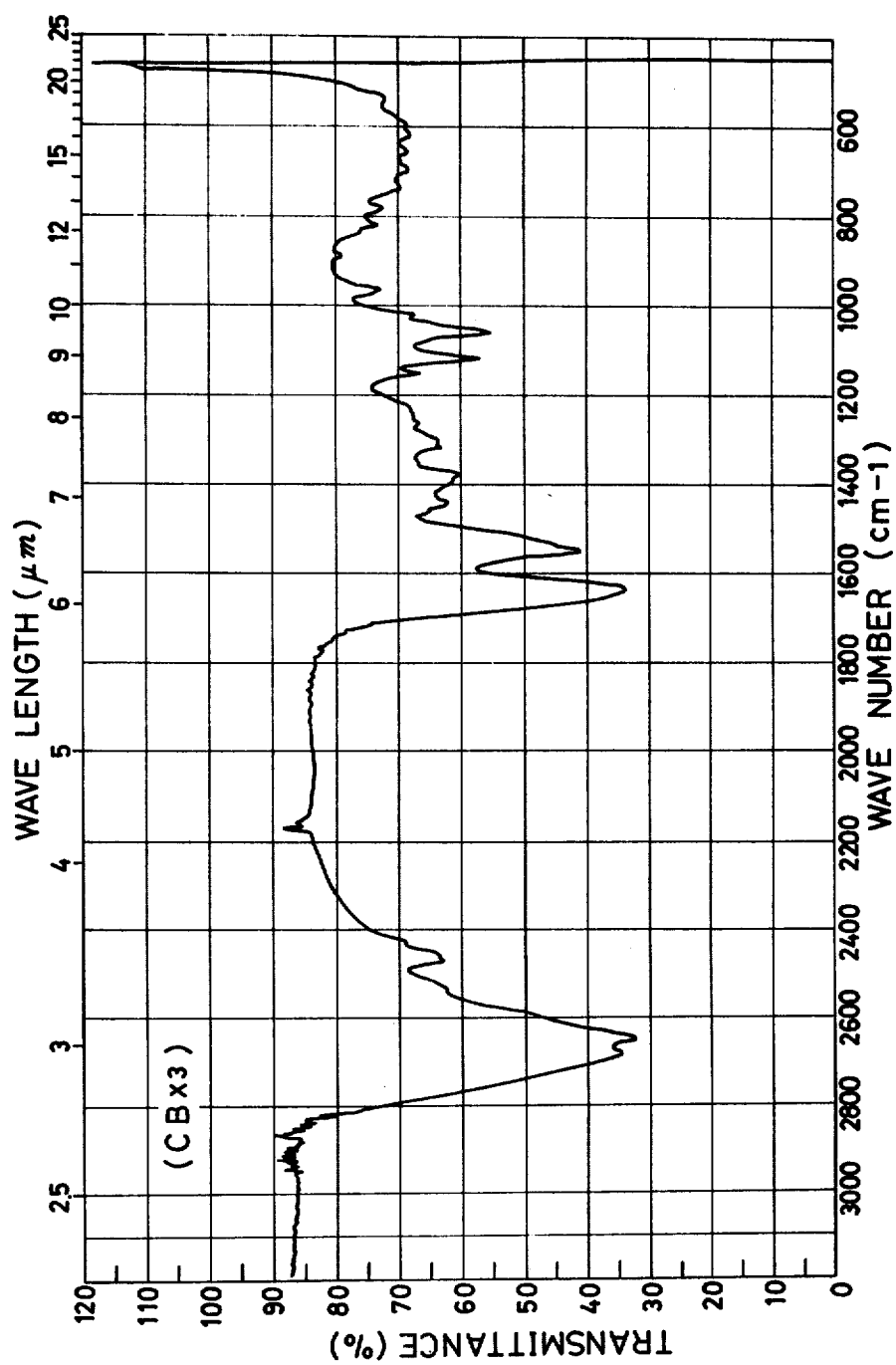
FIG. 4 shows the IR spectrum of $CB_{X3}$ measured in Example 29.

IR measurement of $CB_{X3}$ obtained above was carried out as described in Example 10. The result is shown in FIG. 4.

EXAMPLE 30: (AQUEOUS INJECTIONS)

| | |
|---|---|
| $CB_X$ | 100,000 units |
| Sodium chloride | 9 g |
| Distilled water for injection to make | 1,000 ml |

The $CB_X$ and sodium chloride were weighed and mixed, then dissolved in 500 ml of distilled water for injection, and the total volume was adjusted to 1,000 ml with distilled water for injection. This aqueous solution was filtered under sterile conditions using a membrane filter, and 2 ml each of the filtrate was placed into sterilized glass containers and sealed to prepare aqueous injections.

EXAMPLE 31-33

Procedures similar to those in Example 30 were carried out for $CB_{X1}$, $CB_{X2}$ and $CB_{X3}$ to prepare aqueous injections respectively.

EXAMPLE 34: (LYOPHILIZED INJECTIONS)

| | |
|---|---|
| $CB_X$ | 100,000 units |
| 20% Human serum albumin | 10 ml |
| Sodium chloride | 9 g |

| | |
|---|---|
| -continued | |
| Distilled water for injecton to make | 1,000 ml |

The $CB_X$ and sodium chloride were weighed and mixed, then dissolved in a solution obtained by adding the predetermined amount of the human albumin to 500 ml of distilled water for injection, and the total volume was adjusted to 1,000 ml with distilled water for injection. This solution was filtered under sterile conditions with a membrane filter, and 2 ml each of the filtrate was placed into sterilized glass containers, lyophilized, and sealed to prepare lyophilized powders for injection.

EXAMPLE 35–37

Procedures similar to those in Example 34 were carried out for $CB_{X1}$, $CB_{X2}$ and $CB_{X3}$ to prepare lyophylized powders for injection respectively.

EXAMPLE 38: (EYE DROP)

| | |
|---|---|
| $CB_X$ | 100,000 units |
| Sodium chloride | 5 g |
| Chlorobutanol | 5 g |
| Distilled water for injection to make | 1,000 ml |

The above ingredients were weighed and dissolved in 950 ml of distilled water for injection. The total volume was adjusted to 1,000 ml, and the solution was filtered under sterile conditions using a membrane filter to make an eye drop preparation.

EXAMPLE 39–41

Procedures similar to those in Example 38 were carried out for $CB_{X1}$, $CB_{X2}$ and $CB_{X3}$ to make eye drop preparations respectively.

EXAMPLE 42: (SUPPOSITORIES)

| | |
|---|---|
| $CB_X$ | 100,000 units |
| Polyethylene glycol 1500 | 250 g |
| Polyethylene glycol 4000 | Ca. 750 g |
| | 1,000 g |

The above ingredients were weighed and the whole amounts of the $CB_X$ and polyethlene glycol 1500 and 500 g of the polyethylene glycol 4000 were mixed thoroughly, after which the remaining polyethylene glycol 4000 was added to give the total weight of 1,000 g, further mixed thoroughly and made into 5,000 mg rectal suppositories by the melting method.

EXAMPLE 43–45

Procedures similar to those in Example 42 were carried out for $CB_{X1}$, $CB_{X2}$ and $CB_{X3}$ to prepare rectal suppositories respectively.

EXAMPLE 46: (NASAL DROP)

| | |
|---|---|
| $CB_X$ | 100,000 units |
| Sodium chloride | 5 g |
| Chlorobutanol | 5 g |
| Distilled water to make | 1,000 ml |

The above ingredients were weighed and dissolved in 950 ml of distilled water. The resultant solution was adjusted to the total volume of 1,000 ml with distilled water to prepare a solution for nasal drop.

EXAMPLE 47–49

Procedures similar to those in Example 46 were carried out for $CB_{X1}$, $CB_{X2}$ and $CB_{X3}$ to prepare a solutions for nasal drop respectively.

EXAMPLE 50: (ENTERIC COATED TABLETS)

| | |
|---|---|
| $CB_X$ | 1,000,000 units |
| Lactose | 64 g |
| Potato starch | ca. 30 g |
| Polyvinyl alcohol | 3 g |
| Magnesium stearate | 3 g |
| | 100 g |

The above ingredients were weighed respectively, the whole of the $CB_X$ and lactose and about half amount of the potato starch were mixed; then the remaining potato starch was added to a mixture so as to give the total weight of 94 g; and the mixture was mixed to achieve homogenity. To the resultant mixture was added an aqueous polyvinyl alcohol solution, and granules were prepared by the wet pelletizing method. The granules were dried, mixed with the magnesium stearate, and compressed into 200 mg tablets. The tablets were coated with methyl cellulose phthalate to prepare enteric coated tablets.

EXAMPLE 51–53

Procedures similar to those in Example 50 were carried out for $CB_{X1}$, $CB_{X2}$ and $CB_{X3}$ to prepare enteric coated tablets respectively.

EXAMPLE 54: (OINTMENT)

| | |
|---|---|
| $CB_X$ | 100,000 units |
| Liquid paraffin | 10 g |
| Vaseline (Trademark) | ca. 1,000 g |
| | 1,000 g |

The above ingredients were weighed respectively, then the $CB_X$ was thoroughly kneaded with the liquid paraffin, 500 g of the Vaseline (Trademark) was added thereto, and mixed thoroughly. To the mixture was gradually added the remaining Vaseline (Trademark) to give the total weight of 1,000 g, and the mixture was thoroughly mixed to prepare an ointment.

EXAMPLE 55–57

Procedures similar to those in Example 54 were carried out for $CB_{X1}$, $CB_{X2}$ and $CB_{X3}$ to prepare ointments respectively.

What is claimed is:

1. A substantially purified form of a glycoprotein ($CB_X$) produced from non-established cells or cells of established cell lines of reticulo-endothelial cells, lymphoblasts, leukemia cells or fibroblasts originated from warm-blooded animals, having an anti-tumor effect and having the following properties:
   (a) molecular weight: 12,000–17,000;
   (b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 27-33%, 17-20% of the total sugar being hexoses, 5-7% being hexosamines and 5-6% being sialic acids;

(e) isoelectric point: 4.2-7.3;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 or pH 11.0 at 4° C. for 24 hours or longer and in an aqueous solution of pH 7.0 at 60° C. for 3 hours or longer;

(h) cytotoxicity: it selectively damages tumor cells without substantially damaging normal cells; and (i) differentiation: induces differentiation of tumor cells.

2. A substantially purified form of a glycoprotein ($CB_{X1}$), produced from non-established cells or cells of established cell lines of reticulo-endothelial cells, lymphoblasts, leukemia cells or fibroblasts originated from warm-blooded animals, having an anti-tumor effect and having the following properties:

(a) molecular weight: 70,000-90,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 35-45%, 23-28% of the total sugar being hexoses, 8-11% being hexosamines and 4-6% being sialic acids;

(e) isoelectric point: 4.3-6.2;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 pH 11.0 at 4° C. for 24 hours or longer and in an aqueous solution of pH 7.0 at 60° C. for 3 hours or longer; and (h) cytotoxicity: it selectively damages tumor cells without substantially damaging normal cells.

3. A substantially purified form of a glycoprotein ($CB_{X2}$), produced from non-established cells or cells of established cell lines of reticulo-endothelial cells, lymphoblasts, leukemia cells or fibroblasts originated from warm-blooded animals, having an anti-tumor effect and having the following properties:

(a) molecular weight: 40,000-50,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 30-37%, 20-23% of the total sugar being hexoses, 6-8% being hexosamines and 4-6% being sialic acids;

(e) isoelectric point: 4.2-7.3;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 or pH 11.0 at 4° C. for 24 hours or longer and in an aqueous solution of pH 7.0 at 60° C. for 3 hours or longer; and (h) cytotoxicity: it selectively damaged tumor cells without substantially damaging normal cells.

4. A substantially purified form of a glycoprotein ($CB_{X3}$), produced from non-established cells or cells of established cell lines of reticulo-endothelial cells, lymphoblasts, leukemia cells or fibroblasts originated from warm-blooded animals, having an anti-tumor effect and having the following properties:

(a) molecular weight: 7,000-9,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 8-15%, 6-10% of the total sugar being hexoses, 1-2% being hexosamines and 1-3% being sialic acids;

(e) adsorbability: adsorbable on carboxymethylcellulose in an ion exchange chromatography in 0.05M phosphate buffer (pH 6.4) using carboxymethylcellulose;

(f) stability: stable in an aqueous solution of pH 2.0, pH 7.0 or pH 11.0 at 4° C. for 24 hours or longer and in an aqueous solution of pH 7.0 at 60° C. for 3 hours or longer;

(g) cytotoxicity: it selectively damages tumor cells without substantially damaging normal cells; and (h) the amino acid sequence of the N terminal of its protein portion is Alanine-Alanine-.

5. A process for producing a glycoprotein ($CB_X$) having an anti-tumor effect, comprising:

culturing non-established cells or cells of established cell lines of reticulo-endothelial cells, lymphoblasts, leukemia cells or fibroblasts originated from warm-blooded animals, and isolating glycoproteins from a homogeneous mass or a cultured supernatant of said cultured cells, said isolated glycoproteins having the following properties:

(a) molecular weight: 12,000-17,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 27–33%, 17–20% of the total sugar being hexoses, 5–7% being hexosamines and 5–6% being sialic acids;

(e) isoelectric point: 4.2–7.3;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 or pH 11.0 at 4° C. for 24 hours or longer and in an aqueous solution of pH 7.0 at 60° C. for 3 hours or longer;

(h) cytotoxicity: it selectively damages tumor cells without substantially damaging normal cells; and (i) differentiation: induces differentiation of tumor cells.

6. A process for producing a glycoprotein ($CB_{X1}$) having an anti-tumor effect, comprising:

culturing non-established cells or cells of established cell lines of reticulo-endothelial cells, lymphoblasts, leukemia cells or fibroblasts originated from warm-blooded animals, and isolating glycoproteins from a homogeneous mass or a cultured supernatant of said cultured cells, said isolated glycoproteins having the following properties:

(a) molecular weight: 70,000–90,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 35–45%, 23–28% of the total sugar being hexoses, 8–11% being hexosamines and 4–6% being sialic acids;

(e) isoelectric point: 4.3–6.2;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 or pH 11.0 at 4° C. for 24 hours or longer and in an aqueous solution of pH 7.0 at 60° C. for 3 hours or longer; and (h) cytotoxicity: it selectively damages tumor cells without substantially damaging normal cells.

7. A process for producing a glycoprotein ($CB_{X2}$) having an anti-tumor effect, comprising:

culturing non-established cells or cells of established cell lines of reticulo-endothelial cells, lymphoblasts, leukemia cells or fibroblasts originated from warm-blooded animals, and isolating glycoproteins from a homogeneous mass or a cultured supernatant of said cultured cells, said isolated glycoproteins having the following properties:

(a) molecular weight: 40,000–50,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 30–37%, 20–23% of the total sugar being hexoses, 6–8% being hexosamines and 4–6% being sialic acids;

(e) isoelectric point: 4.2–7.3;

(f) adsorbability: adsorbable on Ulex europeus agglutinin-conjugated Sephadex in 0.01M phosphate buffer (pH 7.2);

(g) stability: stable in an aqueous solution of pH 2.0, pH 7.0 or pH 11.0 at 4° C. for 24 hours or longer and in an aqueous solution of pH 7.0 at 60° C. for 3 hours or longer; and (h) cytotoxicity: it selectively damages tumor cells without substantially damaging normal cells.

8. A process for producing a glycoprotein ($CB_{X3}$) having an anti-tumor effect, comprising:

culturing non-established cells or cells of established cell lines of reticulo-endothelial cells, lymphoblasts, leukemia cells or fibroblasts originated from warm-blooded animals, and isolating glycoproteins from a homogeneous mass or a cultured supernatant of said cultured cells, said isolated glycoproteins having the following properties:

(a) molecular weight: 7,000–9,000;

(b) color reactions: it exhibits a color indicating proteins in the Lowry reaction, exhibits a color indicating peptide bonds and amino acids in the ninhydrin reaction after hydrolysis with hydrochloric acid, and exhibits a color indicating sugars in the phenol-sulfuric acid reaction, the anthrone-sulfuric acid reaction, the indole-sulfuric acid reaction and the tryptophane-sulfuric acid reaction;

(c) appearance and solubility: white powder soluble in water, aqueous sodium chloride and phosphate buffer, and sparingly soluble in benzene, hexane and chloroform;

(d) sugar content: sugar content is 8–15%, 6–10% of the total sugar being hexoses, 1–2% being hexosamines and 1–3% being sialic acids;

(e) adsorbability: adsorbable on carboxymethylcellulose in an ion exchange chromatography in 0.05M phosphate buffer (pH 6.4) using carboxymethylcellulose;

(f) stability: stable in an aqueous solution of pH 2.0, pH 7.0 or pH 11.0 at 4° C. for 24 hours or longer and in an aqueous solution of pH 7.0 at 60° C. for 3 hours or longer;

(g) cytotoxicity: it selectively damages tumor cells without substantially damaging normal cells; and (h) the amino acid sequence of the N terminal of its protein portion is Alanine-Alanine.

9. A process according to claim 5, wherein the source cells are exposed to the action of one or more inducers.

10. A process for producing a glycoprotein having an anti-tumor effect as claimed in claim 6, wherein said cultured cells are exposed to the action of an inducer.

11. A process for producing a glycoprotein having an anti-tumor effect as claimed in claim 7, wherein said cultured cells are exposed to the action of an inducer.

12. A process for producing a glycoprotein having an anti-tumor effect as claimed in claim 8, wherein said cultured cells are exposed to the action of an inducer.

13. A process for producing a glycoprotein having an anti-tumor effect as claimed in claim 9, wherein the inducer is selected from the group consisting of lectins such as phytohemagglutinin, concanavalin A, pokeweed mitogen, lypopolysaccharides, polysaccharides such as phosphomannan, dextran phosphate, endotoxins, microbial cell components, bacteria, viruses, nucleic acids and polynucleotides.

14. A process for producing a glycoprotein having an anti-tumor effect as claimed in claim 10, wherein the inducer is selected from the group consisting of lectins such as phytohemagglutinin, concanavalin A, pokeweed mitogen, lypopolysaccharides, polysaccharides such as phosphomannan, dextran phosphate, endotoxins, microbial cell components, bacteria, viruses, nucleic acids and polynucleotides.

15. A process for producing a glycoprotein having an anti-tumor effect as claimed in claim 11, wherein the inducer is selected from the group consisting of lectins such as phytohemagglutinin, concanavalin A, pokeweed mitogen, lypopolysaccharides, polysaccharides such as phosphomannan, dextran phosphate, endotoxins, microbial cell components, bacteria, viruses, nucleic acids and polynucleotides.

16. A process for producing a glycoprotein having an anti-tumor effect as claimed in claim 12, wherein the inducer is selected from the group consisting of lectins such as phytohemagglutinin, concanavalin A, pokeweed mitogen, lypopolysaccharides, polysaccharides such as phosphomannan, dextran phosphate, endotoxins, microbial cell components, bacteria, viruses, nucleic acids and polynucleotides.

17. A process according to claim 5, wherein the established cell lines are selected from the group consisting of BALL-1, TALL-1, NALL-1, Namalwa, M-7002, B-7101, Flow 7000, JBL, EBV-Sa, EBV-Wa, EBV-HO, BALM2 and CCRF-SB, all of which are of human origin.

18. A process for producing a glycoprotein having an anti-tumor effect as claimed in claim 6, wherein the cells of the established cell lines are selected from the group consisting of BALL-1, TALL-1, NALL-1, Namalwa, M-7002, M-7101, Flow 7000, JBL, EBV-Sa, EBV-Wa, EBV-HO, BALM2 and CCRF-SB, all of which are of human origin.

19. A process for producing a glycoprotein having an anti-tumor effect as claimed in claim 7, wherein the cells of the established cell lines are selected from the group consisting of BALL-1, TALL-1, NALL-1, Namalwa, M-7002, B-7101, Flow 7000, JBL, EBV-Sa, EBV-Wa, EBV-HO, BALM2 and CCRF-SB, all of which are of human origin.

20. A process for producing a glycoprotein having an anti-tumor effect as claimed in claim 8, wherein the cells of the established cell lines are selected from the group consisting of BALL-1, TALL-1, NALL-1, Namalwa, M-7002, B-7101, Flow 7000, JBL, EBV-Sa, EBV-Wa, EBV-HO, BALM2 and CCRF-SB, all of which are of human origin.

21. A process according to claim 5, wherein the established cell lines are selected from the group consisting of mouse BALB/C 3T3, mouse leukemia cells L1210, P388, mouse melanoma clone M-3, rat tumor LLC-WRC 256, and hamster melanoma RPMI 1846, all of which are of non-human warm-blooded animal origin.

22. A process for producing a glycoprotein having an anti-tumor effect as claimed in claim 6, wherein the cells of the established cell lines are selected from the group consisting of mouse BALB/C 3T3, mouse leukemia cells L1210, P388, mouse melanoma clone M-3, rat tumor LLC-WRC 256, and hamster melanoma RPMI 1846, all of which are of non-human warm-blooded animal origin.

23. A process for producing a glycoprotein having an anti-tumor effect as claimed in claim 7, wherein the cells of the established cell lines are selected from the group consisting of mouse BALB/C 3T3, mouse leukemia cells L1210, P388, mouse melanoma clone M-3, rat tumor LLC-WRC 256, and hamster melanoma RPMI 1846, all of which are of non-human warm-blooded animal origin.

24. A process for producing a glycoprotein having an anti-tumor effect as claimed in claim 8, wherein the cells of the established cell lines are selected from the group consisting of mouse BALB/C 3T3, mouse leukemia cells L1210, P388, mouse melanoma clone M-3, rat tumor LLC-WRC 256, and hamster melanoma RPMI 1846, all of which are of non-human warm-blooded animal origin.

25. A process according to claim 5, wherein said cells are cultured in the body of a non-human animal and grown therein prior to isolation of said glycoproteins.

26. A process according to claim 6, wherein said cells are cultured in the body of a non-human animal and grown therein prior to isolation of said glycoproteins.

27. A process according to claim 7, wherein said cells are cultured in the body of a non-human animal and grown therein prior to isolation of said glycoproteins.

28. A process according to claim 8, wherein said cells cultured in the body of a non-human animal and grown therein prior to isolation of said glycoproteins.

29. A process according to claim 5, wherein said cells are cultured in vitro prior to isolation of said glycoproteins.

30. A process according to claim 6, wherein said cells are cultured in vitro prior to isolation of siad glycoproteins.

31. A process according to claim 7, wherein said cells are cultured in vitro prior to isolation of said glycoproteins.

32. A process according to claim 8, wherein said cells are cultured in vitro prior to isolation of said glycoproteins.

33. A process according to claim 5, wherein said cells are cultured in a diffusion chamber through which said animal body fluid medium circulates.

34. A process according to claim 33, wherein said diffusion chamber is inside an animal during the growth of said cultured cells.

35. A process according to claim 6, wherein said cells are cultured in a diffusion chamber through which said animal body fluid medium circulates.

36. A process according to claim 35, wherein said diffusion chamber is inside an animal during the growth of said cultured cells.

37. A process according to claim 7, wherein said cells are cultured in a diffusion chamber through which said animal body fluid medium circulates.

38. A process according to claim 37, wherein said diffusion chamber is inside an animal during the growth of said cultured cells.

39. A process according to claim 8, wherein said cells are cultured in a diffusion chamber through which said animal body fluid medium circulates.

40. A process according to claim 39, wherein said diffusion chamber is inside an animal during the growth of said cultured cells.

41. A process according to claim 25, wherein said cultured cells are further cultured in vitro after being grown in said animal.

42. A process according to claim 26, wherein said cultured cells are further cultured in vitro after being grown in said animal.

43. A process according to claim 27, wherein said cultured cells are further cultured in vitro after being grown in said animal.

44. A process according to claim 28, wherein said cultured cells are further cultured in vitro after being grown in said animal.

45. A process according to claim 33, wherein said cultured cells are further cultured in vitro after being grown in said diffusion chamber.

46. A process according to claim 35, wherein said cultured cells are further cultured in vitro after being grown in said diffusion chamber.

47. A process according to claim 37, wherein said cultured cells are further cultured in vitro after being grown in said diffusion chamber.

48. A process according to claim 39, wherein said cultured cells are further cultured in vitro after being grown in said diffusion chamber.

49. A process according to claim 25, wherein the possibility of immunological reactions of the animals to which cells are transplanted is minimized by exposing the animals to X-rays or by injecting them with immunosuppressive agents.

50. A process according to claim 26, wherein the possibility of immunological reactions of the animals to which cells are transplanted is minimized by exposing the animals to X-rays or by injecting them with immunosuppressive agents.

51. A process according to claim 27, wherein the possibility of immunological reactions of the animals to which cells are transplanted is minimized by exposing the animals to X-rays or by injecting them with immunosuppressive agents.

52. A process according to claim 28, wherein the possibility of immunological reactions of the animals to which cells are transplanted is minimized by exposing the animals to X-rays or by injecting them with immunosuppressive agents.

53. A process according to claim 5, wherein the animals to which cells are transplanted are nude mice.

54. A process according to claim 6, wherein the animals to which cells are transplanted are nude mice.

55. A process according to claim 7, wherein the animals to which cells are transplanted are nude mice.

56. A process according to claim 8, wherein the animals to which cells are transplanted are nude mice.

57. A process according to claim 5, wherein the non-established cells are selected from the group consisting of macrophages and human lymphocytes.

58. A process according to claim 6, wherein the non-established cells are selected from the group consisting of lymphocytes and macrophages.

59. A process for producing a glycoprotein having an anti-tumor effect as claimed in claim 7, wherein the non-established cells are selected from the group consisting of macrophages and lymphocytes.

60. A process for producing a glycoprotein having an anti-tumor effect as claimed in claim 8, wherein the non-established cells are selected from the group consisting of macrophages and lymphocytes.

* * * * *